United States Patent
Lee et al.

(10) Patent No.: US 11,007,177 B2
(45) Date of Patent: May 18, 2021

(54) COMPOSITIONS COMPRISING A COMBINATION OF A SUBSTITUTED FLAVONOID AND A SUBSTITUTED INDOLE FOR TREATING OCULAR DISEASES

(71) Applicant: University of Macau, Macau (CN)

(72) Inventors: Ming Yuen Lee, Macau (CN); TatFong Ng, Revere, MA (US)

(73) Assignee: UNIVERSITY OF MACAU, Macau (CN)

( * ) Notice: Subject to any disclaimer, the term of this patent is extended or adjusted under 35 U.S.C. 154(b) by 0 days.

(21) Appl. No.: 15/753,707

(22) PCT Filed: Aug. 24, 2016

(86) PCT No.: PCT/IB2016/001341
§ 371 (c)(1),
(2) Date: Feb. 20, 2018

(87) PCT Pub. No.: WO2017/033060
PCT Pub. Date: Mar. 2, 2017

(65) Prior Publication Data
US 2018/0280348 A1  Oct. 4, 2018

Related U.S. Application Data

(60) Provisional application No. 62/209,220, filed on Aug. 24, 2015.

(51) Int. Cl.
*C07D 209/34* (2006.01)
*C07D 311/22* (2006.01)
*A61K 31/404* (2006.01)
*A61K 31/352* (2006.01)
*C07D 405/14* (2006.01)
*A61K 9/00* (2006.01)
*A61K 47/02* (2006.01)
*A61K 9/08* (2006.01)

(52) U.S. Cl.
CPC .......... *A61K 31/404* (2013.01); *A61K 9/0048* (2013.01); *A61K 31/352* (2013.01); *C07D 405/14* (2013.01); *A61K 9/08* (2013.01); *A61K 47/02* (2013.01)

(58) Field of Classification Search
CPC .......................... C07D 209/34; C07D 311/22
USPC .......................................... 548/491; 549/403
See application file for complete search history.

(56) References Cited

FOREIGN PATENT DOCUMENTS

| | | |
|---|---|---|
| IN | 201302049 | 1/2015 |
| WO | WO 2007/075911 | 7/2007 |
| WO | WO 2008/150085 | 12/2008 |

*Primary Examiner* — Douglas M Willis
(74) *Attorney, Agent, or Firm* — Margaret B. Brivanlou; King & Spalding LLP

(57) ABSTRACT

Disclosed are compositions and methods for treatment of a disease or disorder of the eye and adnexa of the eye, including dry eye disease and Sjögren's syndrome, by administering a composition comprising an indole and a flavonoid either as an admixture or as a synthetic heterodimer thereof.

19 Claims, 11 Drawing Sheets

Specification includes a Sequence Listing.

COMPOSITIONS COMPRISING A COMBINATION OF A SUBSTITUTED FLAVONOID AND A SUBSTITUTED INDOLE FOR TREATING OCULAR DISEASES

FIELD

The present invention relates to treatment of a disease or disorder of the eye and adnexa of the eye in an animal subject, including a human being. More particularly, this invention relates to methods for treating ocular diseases and disorders associated with ocular surface inflammation, such as, dry eye disease and Sjögren's syndrome, by administering a composition of the invention.

BACKGROUND

Dry eye disease is a multifactorial disorder of the tears and ocular surface characterized by symptoms of dryness and irritation. Although the pathogenesis of dry eye disease is not fully understood, it is recognized that inflammation has a prominent role in the development and propagation of this debilitating condition. Factors that adversely affect tear film stability and osmolarity can induce ocular surface damage and initiate an inflammatory cascade that generates innate and adaptive immune responses. These immunoinflammatory responses lead to further ocular surface damage and the development of a self-perpetuating inflammatory cycle.

Dry eye disease (DED), also known as keratoconjunctivitis sicca, is a multifactorial disorder of the tears and ocular surface. Common symptoms of DED include dryness, irritation, foreign body sensation, light sensitivity, and itching. It is estimated that almost 5 million Americans 50 years and older have DED, and millions more experience episodic symptoms of dry eye; of these, approximately two-thirds are women. The prevalence of DED rises dramatically with increasing age, and as older populations grow, so too will the burden of DED-associated morbidity.

Sjögren's syndrome is an autoimmune disease that causes the destruction of the tear glands and results in dry eye. The exact etiology of Sjögren's syndrome remains unknown and is believed to be multifactorial. The immunopathogenesis of Sjögren's syndrome is associated with increased levels of Th1 inflammatory effectors known to produce cytokines like IFN-γ and TNF-α as well as Th17 effectors associated with chronic inflammation and characterized by expression of IL-17A and IL-6 in the periphery and exocrine glands (Nguyen et al., 2008, Arthritis Rheum 58: 734-743; van Woerkom et al., 2005, Ann Rheum Dis 64: 1474-1479).

Improved therapies that address ocular inflammation in these and other indications are needed.

SUMMARY

The present invention relates to methods and compositions for treating, preventing, or ameliorating the symptoms of a disease or disorder of the eye and adnexa of the eye (including eyelids and lacrimal apparatus of the eye), particularly associated with surface inflammation of the eye and/or tear ducts; the composition comprising a therapeutically effective amount of i) an indole and ii) a flavonoid, wherein the indole and flavonoid are present as an admixture or as a synthetic heterodimer described herein. In certain embodiments, the composition comprises a mixture of the indole and the flavonoid. In specific embodiments, the indole is indirubin-3'-oxime (I3O) and the flavonoid is quercetin. In alternative embodiments, the indole is I3O and the flavonoid is baicalein. In alternative embodiments, the indole and the flavonoid are administered in separate pharmaceutical compositions either at the same time or on different dosing schedules.

The therapeutically effective amount provided in the composition includes amounts of the indole and the flavonoid that, individually are not therapeutically effective, but in combination have a therapeutic effect. In certain embodiments, the therapeutic effect of the indole and the flavonoid are additive, and, in preferred embodiments, the therapeutic effect of the indole and the flavonoid are synergistic (i.e., greater than additive).

Embodiments of the composition include dietary supplements, nutraceutical compositions, medical foods, and animal feeds that treat, prevent or ameliorate the symptoms of a disease or disorder of the eye and adnexa of the eye (including eyelids and lacrimal apparatus of the eye), particularly associated with surface inflammation of the eye and/or tear ducts. Preferably, composition or compositions comprising the indole and the flavonoid are formulated as eye drops.

The invention is also directed to methods of treating, preventing, or ameliorating the symptoms of a disease or disorder of the eye and adnexa of the eye (including eyelids and lacrimal apparatus of the eye), particularly associated with surface inflammation of the eye and/or tear duct by administering a composition comprising a therapeutically effective amount of i) an indole and ii) a flavonoid, wherein the indole and flavonoid are present as a mixture or as a synthetic heterodimer described herein.

DETAILED DESCRIPTION

Figure 1:
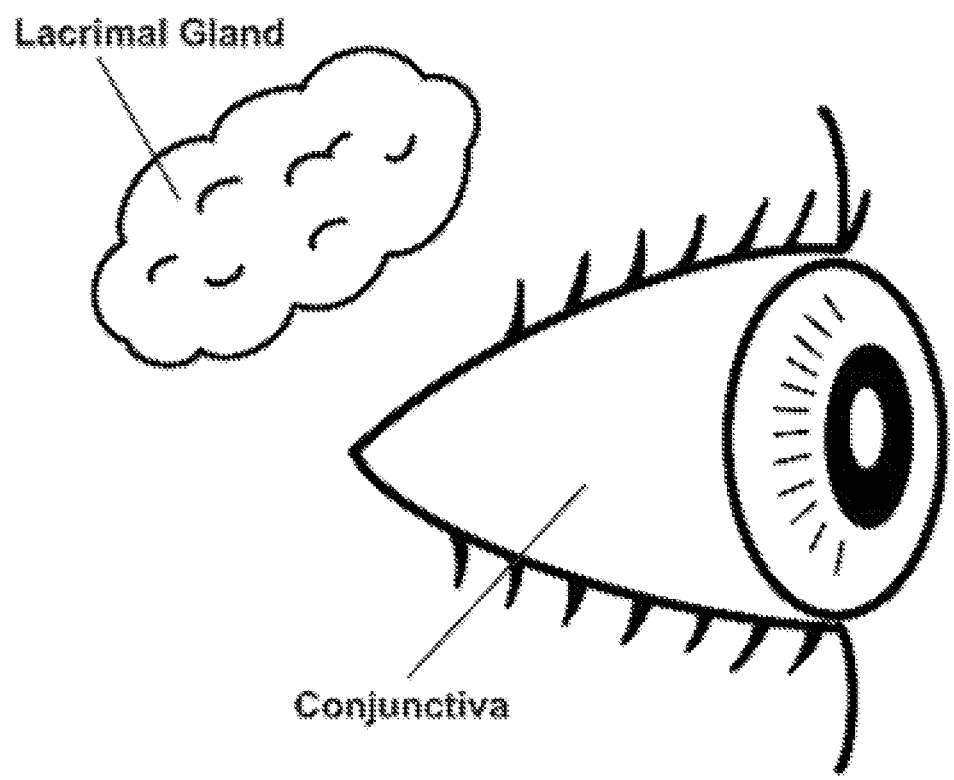
FIG. 1 is an illustration of the adnexa of the eye showing the lacrimal gland and conjunctiva.
Figure 2:
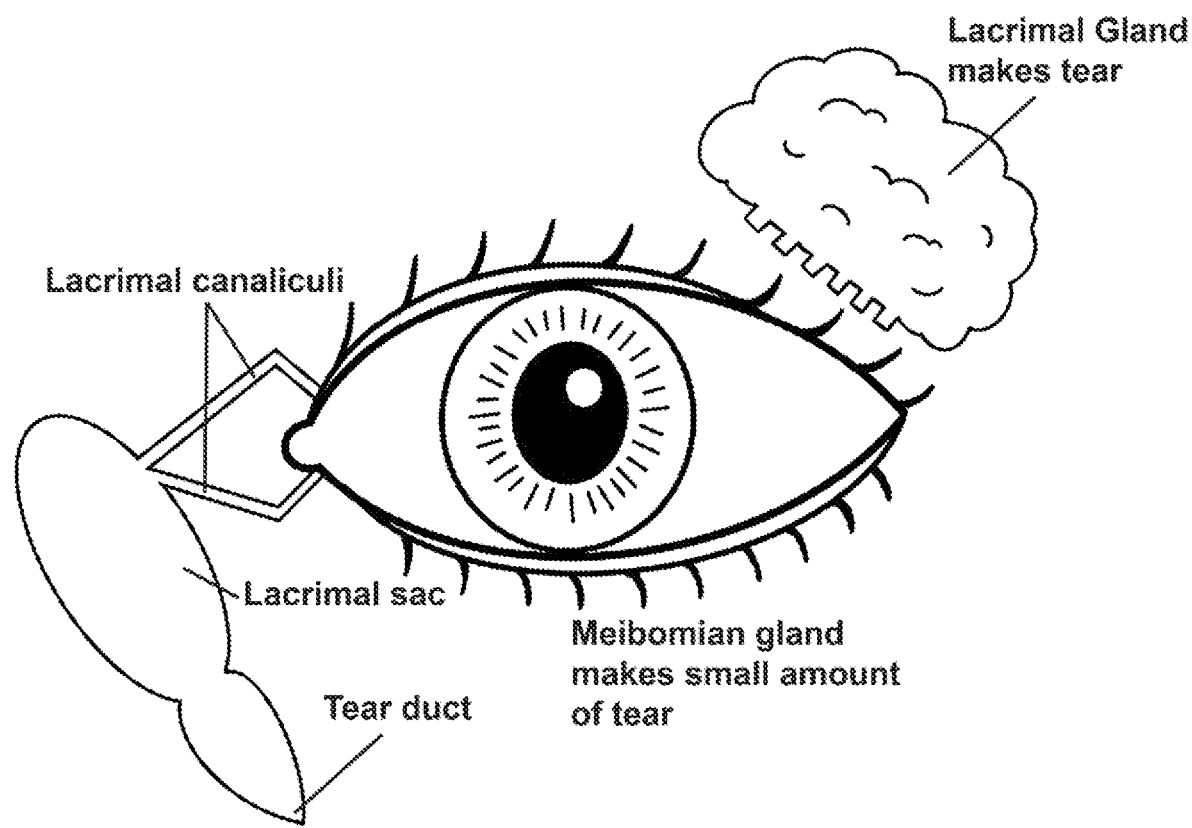
FIG. 2 is an illustration of the adnexa of the eye showing the lacrimal gland, lacrimal ducts (or canaliculi), tear sac, and tear duct (or nasal-lacrimal duct), and conjunctiva.

The inventors have discovered that administration of a combination of an indole and a flavonoid shows greater efficacy than either the indole or the flavonoid alone in alleviating ocular inflammation, as assessed by indicators of ocular disease in in vitro and murine models. Accordingly, provided are pharmaceutical compositions comprising a combination of an indole and a flavonoid for use in treating ocular inflammation and methods of treating, preventing and ameliorating the symptoms of indications involving ocular inflammation with a combination of an indole and a flavonoid.

Indoles

An indole is an aromatic heterocyclic organic compound. It has a bicyclic structure, consisting of a six-membered benzene ring fused to a five-membered nitrogen-containing pyrrole ring. Indoles are widely distributed in the natural environment and can be produced by a variety of bacteria. Indole backbone and IUPAC numbering sequence:

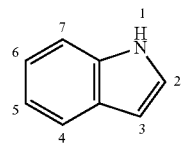

Indole derivatives (or simply, indoles) suitable for use with the disclosed compositions and methods of the invention include one or more indoles characterized by a chemical formula according to Formula 1 or Formula 2, illustrated below:

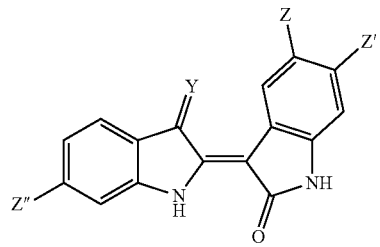

Formula 1

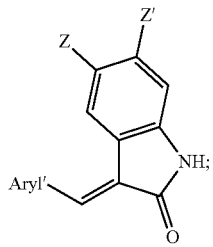

Formula 2 wherein Y is selected from NH or NOH.

Z, Z' and Z" are independently selected from H, Cl, Br and I; in certain embodiments, at least one of Z, Z' and Z" is selected from Cl, Br and I; in alternative embodiments, at least two of Z, Z' and Z" are selected from Cl, Br and I.

Aryl' is a phenyl group substituted by one or more substituents selected from the group consisting of: hydrogen, halogen, hydroxyl, $C_{1-3}$ alkyl groups, $C_{1-3}$ ester groups, amines, $C_{1-3}$ alkyl substituted amines, aryl substituted amines, carboxylate groups, $C_{1-3}$ alkyl carboxylate esters, $C_{1-3}$ alkyl amides, sulfonates, $C_{1-3}$ alkyl sulfonates, including derivatives of these groups and equivalents thereof known in the art that do not destroy the efficacy of the disclosed formulations. Specific examples include wherein Aryl' is: phenyl, methylbenzene, dimethylbenzene, phenol, methyl phenol, benzenamine, diphenylamine, benzenecarboxylic acid, benzenecarboxylic acid ester, benzenesulfonate chlorophenyl or bromophenyl.

The indole suitable for use with the disclosed compositions and methods of the invention include natural indole containing compounds including indirubin and its analogues such as indigo, isoindigo, indirubin E804, and indirubin-3'-oxime (I3O), indirubin-3'-(2,3 dihydroxypropyl)-oximether (E804), 6-bromo-indirubin-3'-oxime, 5-iodo-indirubin-3'-oxime, 5-5'-dibromo-indirubin indirubin-5-sulphonate such as 5-sulfonic acid-indirubin-3'-oxime illustrated below. Also included are synthetic indoles such as sunitinib, SU4312 and SU5416, also illustrated below.

TABLE 1

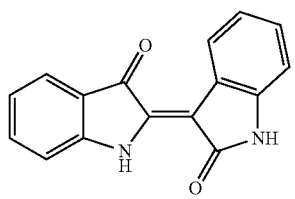

indirubin

TABLE 1-continued

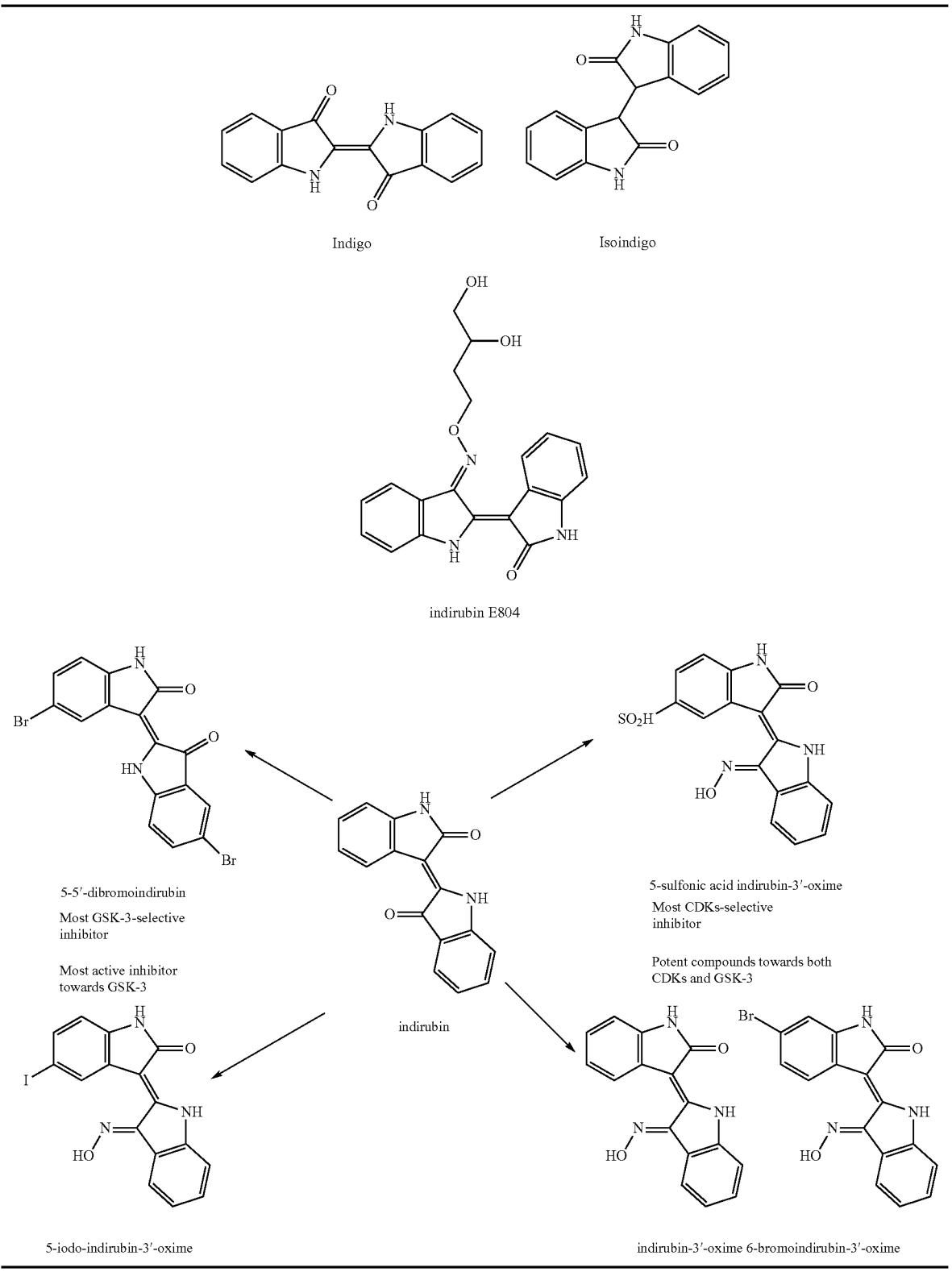

Indirubins are a family of bis-indoles isolated from many different sources such as indigo-producing plants, several species of gastropod mollusks, urine, e.g., from humans, as well as some bacterial strains.

The indoles suitable for use with the disclosed compositions and methods of the invention may have particularly potent activity in inhibiting CDK2, and GSK-3. Such activity is associated with a pharmacological effect in cancer and neurodegenerative disease.

Recent studies indicate that not only the above-mentioned naturally occurring compounds such as indirubin and I3O, but also several synthetic indole heterocyclic compounds/drugs such as sunitinib, SU4312 and SU5416, possess utility in the combinations of the invention.

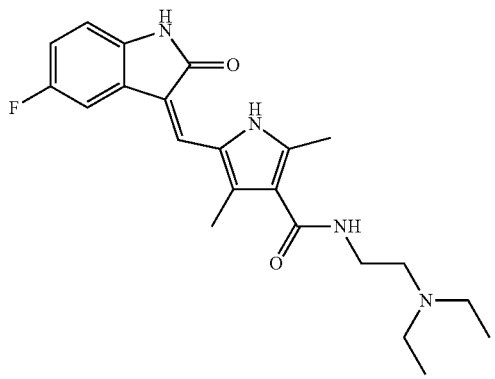

Sunitinib

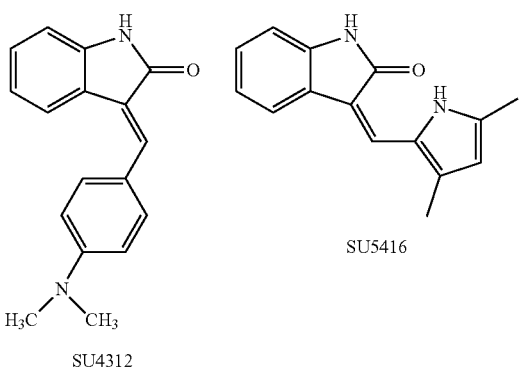

SU4312

SU5416

Flavonoids

Flavonoids (or bioflavonoids) are a class of plant secondary metabolites which have received much attention for their potential medicinal properties associated with reduced risk of certain age related and human chronic diseases supported by epidemiological studies. There is experimental evidence associating flavonoids with anti-allergic, anti-inflammatory, antimicrobial and anti-cancer properties and demonstrating that flavonoids are strong antioxidants. The molecular mechanism of these properties still remains to be elucidated.

Flavonoids are low molecular weight phenylbenzopyrones and belong to the large group a group of vegetable chemical substances, the polyphenols, which are characterised by the presence of more than one phenol group per molecule. The group of flavonoids includes more than 5000 natural flavonoids which are categorised into five subgroups according to their chemical structure: flavonols, flavones, flavanones, flavan-3-ols and the anthocyanidins. Flavonoids have the general structure of a 15-carbon skeleton, which consists of two phenyl rings (A and B) and heterocyclic ring (C). This carbon structure can be abbreviated C6-C3-C6. The flavonoid backbone and IUPAC numbering sequence is shown below:

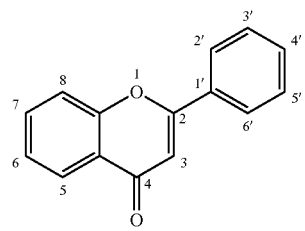 [SMILES: O=c1cc(-c2ccccc2)oc2ccccc12]

Flavonoids suitable for use with the disclosed compositions and methods of the invention include one or more flavonoids characterized by a chemical formula according to Formula 3 illustrated below:

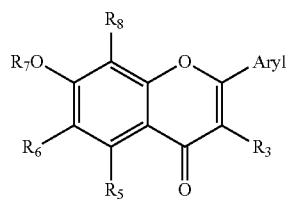

Formula 3 wherein $R_3$, $R_5$, $R_6$ and $R_8$ are independently selected from H, OH, $OCH_3$, and OP wherein P is a protecting group; $R_7$ is selected from H and P wherein P is a protecting group. Suitable protecting groups are known to those in the art and include tert-carbonyl (t-BuCO—), benzoyl (PhCO—), and acetyl (MeCO—), chloroacetyl ($ClCH_2CO$—) groups. The phenyl moiety may include one or more substituents at any position on the phenyl ring, in particular, the substituents include OH and $OCH_3$.

Flavonoids suitable for use with the disclosed compositions and methods of the invention include flavonols where the $R_3$ of the flavonoid is an OH group. The basic flavonol backbone formula is shown below. Flavonol derivatives include further substitutions at other positions of the backbone:

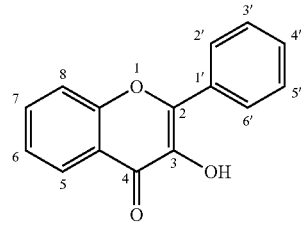 [SMILES: O=c1c(O)c(-c2ccccc2)oc2ccccc12]

Specific flavonoids suitable for use with the disclosed compositions and methods include quercetin, baicalein, chrysin, kaempferol, wogonin, apigenin, luteolin, fisetin, galangin, myricetin, scutellarein, morin; azaleatin, gossypetin, kaempferide, isorhamnetin, natsudaidain, pachypodol, rhamnazin and rhamnetin, as illustrated in Tables 2 and 3 below.

TABLE 2
Chemical Formulas of Flavonoids
| Flavones | Flavonols |
|---|---|
| 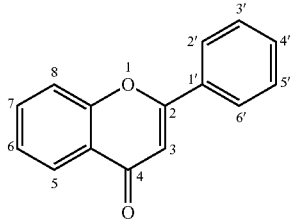<br>flavonoid backbone | 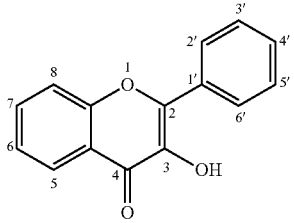<br>flavonol backbone |
| 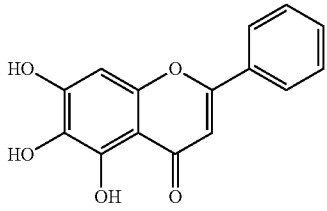<br>Baicalein | 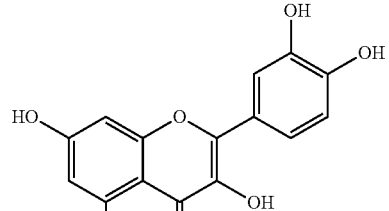<br>Quercetin |
| 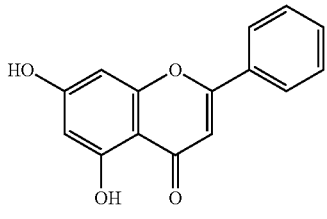<br>Chrysin | 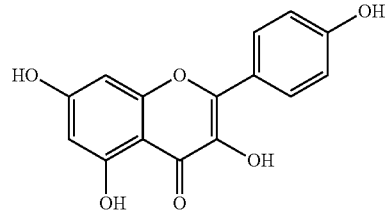<br>Kaempferol |
| 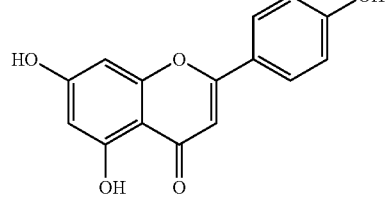<br>Apigenin | 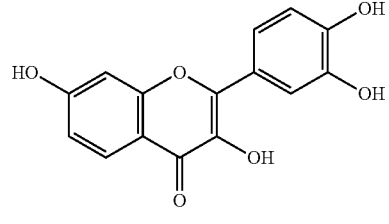<br>Fisetin |

TABLE 2-continued

Chemical Formulas of Flavonoids

| Flavones | Flavonols |
|---|---|

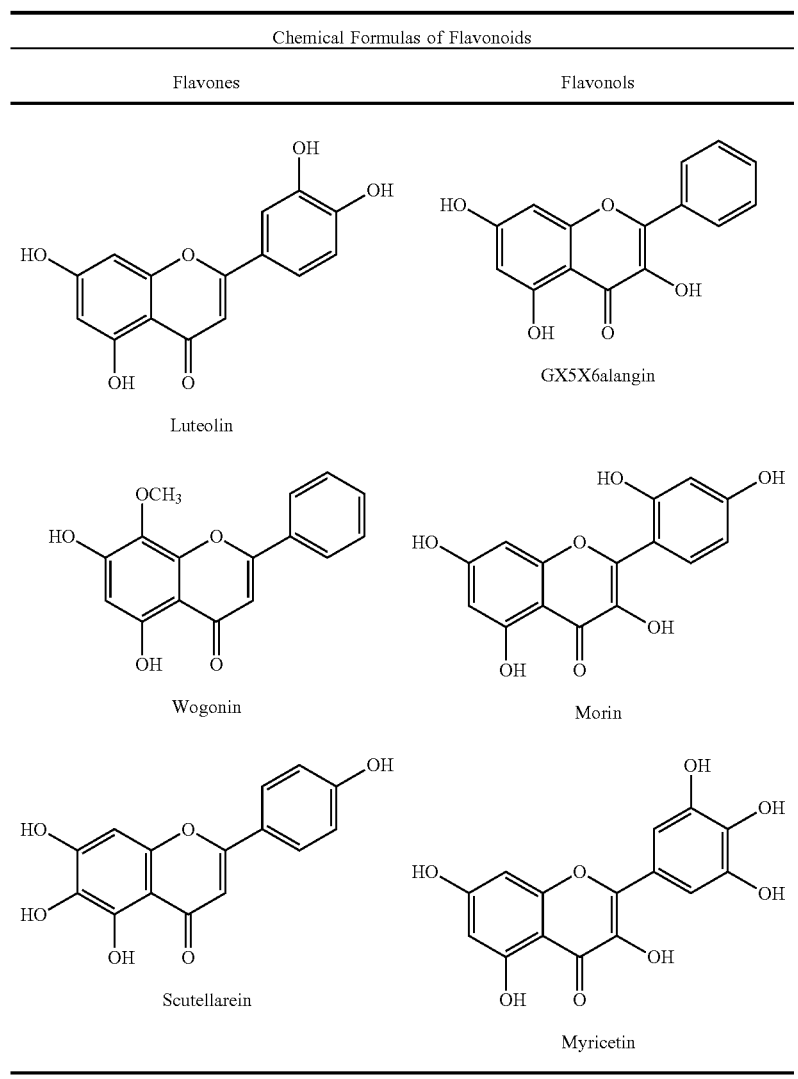

Luteolin

GX5X6alangin

Wogonin

Morin

Scutellarein

Myricetin

TABLE 3

Other flavonoids suitable for use with compositions of the invention

| Name | IUPAC name | 5 | 6 | 7 | 8 | 2' | 3' | 4' | 5' | 6' |
|---|---|---|---|---|---|---|---|---|---|---|
| Azaleatin | 2-(3,4-dihydroxyphenyl)-3,7-dihydroxy-5-methoxychromen-4-one | OCH₃ | H | OH | H | H | H | OH | OH | H |
| Gossypetin | 2-(3,4-dihydroxyphenyl)-3,5,7,8-tetrahydroxychromen-4-one | OH | H | OH | OH | H | OH | OH | H | H |
| Kaempferide | 3,5,7-trihydroxy-2-(4-methoxyphenyl)chromen-4-one | OH | H | OH | H | H | H | OCH₃ | H | H |
| Isorhamnetin | 3,5,7-trihydroxy-2-(4-hydroxy-3-methoxyphenyl)chromen-4-one | OH | H | OH | H | H | OCH₃ | OH | H | H |
| Natsudaidain | 2-(3,4-dimethoxyphenyl)-3-hydroxy-5,6,7,8-tetramethoxychromen-4-one | OCH₃ | OCH₃ | OCH₃ | OCH₃ | H | H | OCH₃ | OCH₃ | H |
| Pachypodol | 5-hydroxy-2-(4-hydroxy-3-methoxyphenyl)-3,7-dimethoxychromen-4-one | OH | H | OCH₃ | H | H | H | OH | OCH₃ | H |
| Rhamnazin | 3,5-dihydroxy-2-(4-hydroxy-3-methoxyphenyl)-7-methoxychromen-4-one | OH | H | OCH₃ | H | H | OCH₃ | OH | H | H |
| Rhamnetin | 2-(3,4-dihydroxyphenyl)-3,5-dihydroxy-7-methoxychromen-4-one | OH | H | OCH₃ | H | H | OH | OH | H | H |

In alternative embodiments, the composition comprises a synthetic heterodimer consisting of an indole and a flavonoid synthetically conjugated together, for example, according to the chemical formulas of Formula 4 or Formula 5, below:

Formula 4

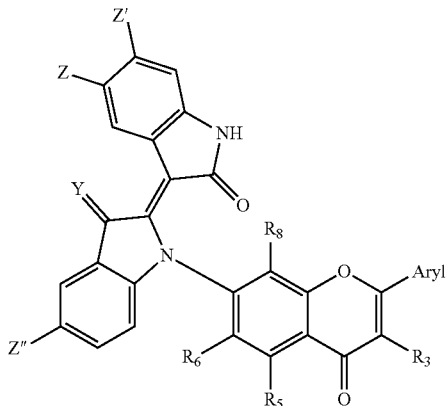

Formula 5

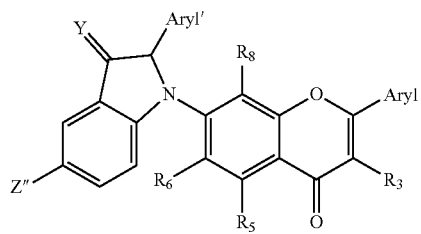

wherein Y is selected from NH or NOH;

Z, Z' and Z" are independently selected from H, Cl, Br and I; in certain embodiments, at least one of Z, Z' or Z" is selected from Cl, Br and I; in additional embodiments, at least two of Z, Z' or Z" are selected from Cl, Br and I;

$R_3$, $R_5$, $R_6$ and $R_8$ are independently selected from H, OH, $OCH_3$, and OP wherein P is a protecting group; in certain embodiments, at least one of $R_3$, $R_5$, $R_6$ and $R_8$ is selected from OH, $OCH_3$, and OP; in additional embodiments, at least two of $R_3$, $R_5$, $R_6$ and $R_8$ are selected from OH, $OCH_3$, and OP; and Aryl is phenyl group substituted by one or more selected from the group consisting of: hydrogen, halogen, hydroxyl, $C_{1-3}$ alkyl groups, $C_{1-3}$ ester groups, amines, $C_{1-3}$ alkyl substituted amines, aryl substituted amines, carboxylate groups, $C_{1-3}$ alkyl carboxylate esters, $C_{1-3}$ alkyl amides, sulfonates, $C_{1-3}$ alkyl sulfonates including derivatives of these groups and including other substituents known in the art that do not destroy the efficacy of the disclosed formulations. Specific examples include wherein Aryl is methylbenzene, dimethylbenzene, phenol, methyl phenol, benzenamine, diphenylamine, benzenecarboxylic acid, benzenecarboxylic acid ester, benzenesulfonate.

Synthesis of New Heterodimers

Preparation of an Hydroxyl Protected Flavonoid Starting Material

The hydroxyl groups on the flavonoid starting material may be protected according to any method known by a person of skill in organic synthesis. In one embodiment, a flavonoid having a chemical formula according to Formula 3 illustrated above and a molar excess of a protecting reagent, such as 4-bromo-butyric acid, per hydroxyl group to be protected on the flavonoid (e.g., in a molar ratio of 1.2 mol protecting agent per 1 mol eq. hydroxyl group is dissolved in dry organic solvent such as DMF, with a base such as $K_2CO_3$. NaI is then added to the solution which is then heated under a $N_2$ atmosphere at around 95° C. for 2 hours while stirring. The reaction mixture is poured into water (50 ml) and the organic materials are extracted into ethyl acetate (3×20 ml). The extract is washed with $H_2O$ (5 ml) and the organic fraction is isolated, dried and the solvent is evaporated in vacuo. The residue is then purified, for example, by column chromatography on silica gel using hexane-acetone to elute the desired protected indole.

Preparation of Indole-flavonoid Heterodimer Product

The coupling reaction of the protected flavonoid with a free amine of the indole may be according to any coupling reaction known to an organic chemist of ordinary skill known to achieve this type of coupling. In particular, dehydration coupling schemes are preferred.

In a particular embodiment, the protected flavonoid and an indole having a chemical formula according to Formula 1 or Formula 2 illustrated above are combined in approximately equal molar amounts and dissolved in a dry organic solvent, e.g., THF, and a molar excess of HCl, e.g., about 1.2 eq EDC HCl, is added to this solution which is then stirred overnight. THF is removed under vacuum. The remaining material is extracted, e.g., with ethyl acetate and water, the organic fraction is isolated, dried and then the solvent is evaporated under vacuum. The resulting residue is then purified by methods familiar to those of ordinary skill in organic synthesis, for example, by column chromatography on silica gel using hexane-acetone to elute Product 1a and Product 1b identified in Scheme 1 or to elute product 2 identified in Scheme 2, below. Product 1a and Product 1b can be purified and isolated according to known methods in the chemical arts.

Generic Reaction Scheme 1

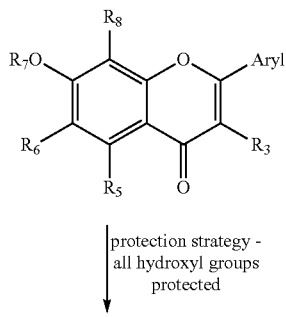

protection strategy - all hydroxyl groups protected

Protected flavonoid of Formula 3

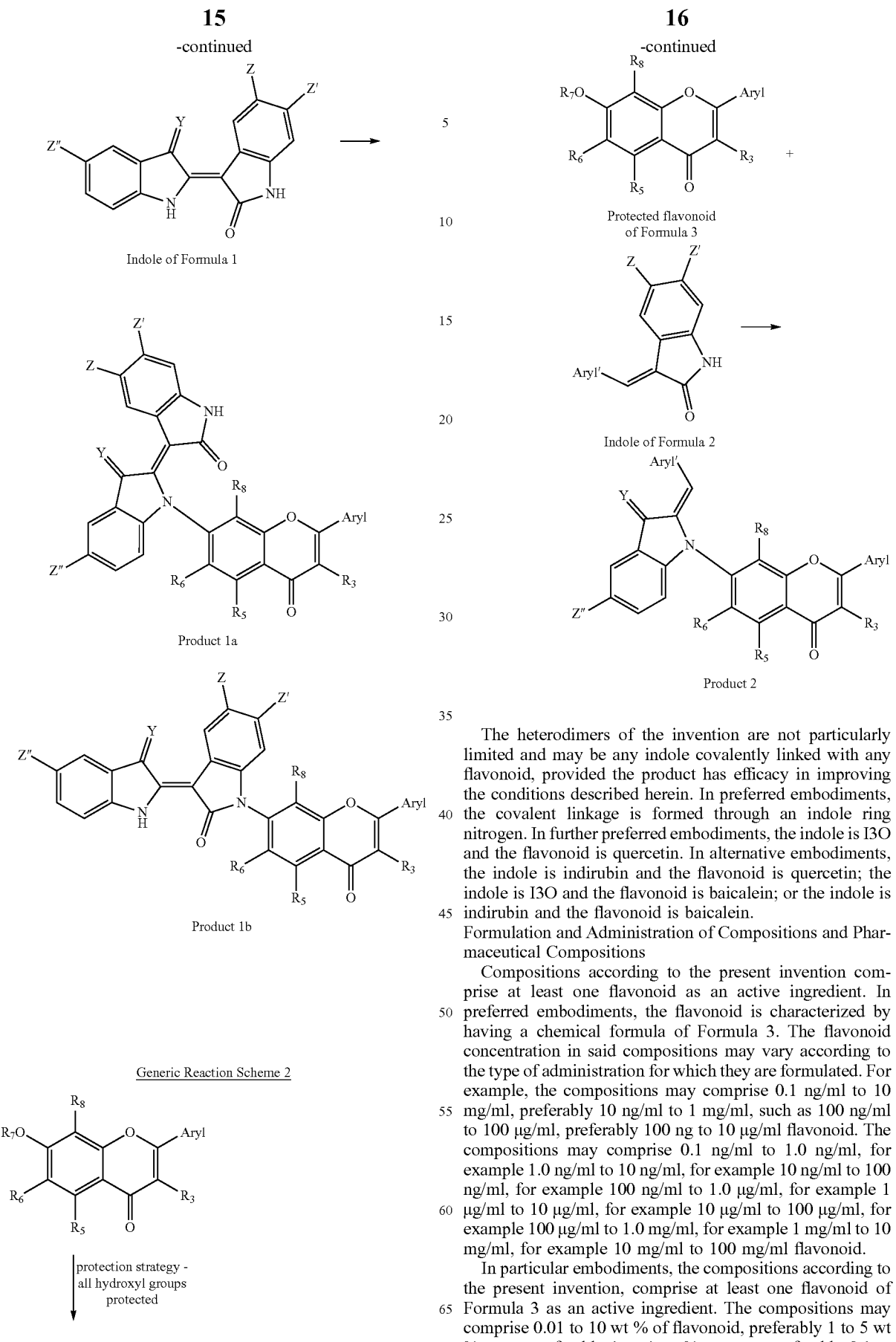

The heterodimers of the invention are not particularly limited and may be any indole covalently linked with any flavonoid, provided the product has efficacy in improving the conditions described herein. In preferred embodiments, the covalent linkage is formed through an indole ring nitrogen. In further preferred embodiments, the indole is I3O and the flavonoid is quercetin. In alternative embodiments, the indole is indirubin and the flavonoid is quercetin; the indole is I3O and the flavonoid is baicalein; or the indole is indirubin and the flavonoid is baicalein.

Formulation and Administration of Compositions and Pharmaceutical Compositions

Compositions according to the present invention comprise at least one flavonoid as an active ingredient. In preferred embodiments, the flavonoid is characterized by having a chemical formula of Formula 3. The flavonoid concentration in said compositions may vary according to the type of administration for which they are formulated. For example, the compositions may comprise 0.1 ng/ml to 10 mg/ml, preferably 10 ng/ml to 1 mg/ml, such as 100 ng/ml to 100 μg/ml, preferably 100 ng to 10 μg/ml flavonoid. The compositions may comprise 0.1 ng/ml to 1.0 ng/ml, for example 1.0 ng/ml to 10 ng/ml, for example 10 ng/ml to 100 ng/ml, for example 100 ng/ml to 1.0 μg/ml, for example 1 μg/ml to 10 μg/ml, for example 10 μg/ml to 100 μg/ml, for example 100 μg/ml to 1.0 mg/ml, for example 1 mg/ml to 10 mg/ml, for example 10 mg/ml to 100 mg/ml flavonoid.

In particular embodiments, the compositions according to the present invention, comprise at least one flavonoid of Formula 3 as an active ingredient. The compositions may comprise 0.01 to 10 wt % of flavonoid, preferably 1 to 5 wt %, more preferably 1 to 4 wt %, or most preferably 0.1 to 2% by weight of the composition. In particularly preferred embodiments, the flavonoid is quercetin or baicalein and the composition is formulated for topical delivery, e.g., into the eye.

Compositions according to the present invention further comprise at least one indole as an active ingredient. In preferred embodiments, the indole is characterized by having a chemical formula of Formula 1 or Formula 2. The concentration of indole in said compositions may vary according to the type of administration they are formulated for. The compositions may comprise 0.1 ng/ml to 10 mg/ml, preferably 10 ng/ml to 1 mg/ml, such as 100 ng/ml to 100 µg/ml, preferably 100 ng to 10 µg/ml indole. The compositions may comprise 0.1 ng/ml to 1.0 ng/ml, for example 1.0 ng/ml to 10 ng/ml, for example 10 ng/ml to 100 ng/ml, for example 100 ng/ml to 1.0 µg/ml, for example 1 µg/ml to 10 µg/ml, for example 10 µg/ml to 100 µg/ml, for example 100 µg/ml to 1.0 mg/ml, for example 1 mg/ml to 10 mg/ml, for example 10 mg/ml to 100 mg/ml indole. In particular embodiments, the compositions according to the present invention comprise at least one indole of formula 1 or 2 as an active ingredient. The compositions may comprise 0.01 to 10 wt % of indole, preferably 1 to 5 wt %, more preferably 1 to 4 wt %, or most preferably 0.1 to 2% by weight of the composition. In particularly preferred embodiments, the indole is indirubin or IO3 and the composition is formulated for topical delivery, e.g., into the eye.

In particular embodiments, the compositions according to the present invention comprise at least one synthetic heterodimer comprising a flavonoid and an indole as an active ingredient. In preferred embodiments, the synthetic heterodimer is characterized by having a chemical formula of Formula 4 or Formula 5. The concentration of heterodimer in said compositions may vary according to the type of administration they are formulated for. The compositions may comprise 0.1 ng/ml to 10 mg/ml, preferably 10 ng/ml to 1 mg/ml, such as 100 ng/ml to 100 µg/ml, preferably 100 ng to 10 µg/ml of the synthetic heterodimer. The compositions may comprise 0.1 ng/ml to 1.0 ng/ml, for example 1.0 ng/ml to 10 ng/ml, for example 10 ng/ml to 100 ng/ml, for example 100 ng/ml to 1.0 µg/ml, for example 1 µg/ml to 10 µg/ml, for example 10 µg/ml to 100 µg/ml, for example 100 µg/ml to 1.0 mg/ml, for example 1 mg/ml to 10 mg/ml, for example 10 mg/ml to 100 mg/ml of the synthetic heterodimer.

In particular embodiments, compositions according to the present invention comprise at least one indole of Formula 1 or Formula 2 and at least one flavonoid of Formula 3 wherein the indole and the flavonoid are present in a molar ratio in the range of from, 1000:1 to 1:1000.

In additional embodiments, compositions according to the present invention comprise at least one heterodimer of an indole and a flavonoid as an active ingredient. The compositions may comprise 0.01 to 10 wt % of heterodimer, preferably 1 to 5 wt %, more preferably 1 to 4 wt %, or most preferably 0.1 to 2% by weight of the composition. Optionally, the composition comprising a heterodimer may further comprise an indole, a flavonoid, or a mixture of both.

In certain embodiments, a composition in accordance with the present invention includes other active agents known in the art to be useful in the treatment of ocular disease, ocular surface inflammation, destruction and damage to tear glands, Sjögren's syndrome and dry eye disease.

According to the present invention "a pharmaceutical effective dosage" of the composition refers to the amount necessary to induce the desired biological effect on the subject in need of treatment.

The composition may be formulated in a number of different manners, depending on the purpose of the particular composition/pharmaceutical composition and the type of administration. It is well within the scope of a person skilled in the arts to formulate compositions that are in accord with the preferred type of administration, such as topically, orally or parenterally.

One preferred embodiment of the present invention is to provide a composition formulated for topical application on a local, superficial and restricted area in the eye and the adnexa of the eye, also referred to as an ophthalmic composition. In said above-mentioned embodiment, it is preferred that the composition is formulated as an ointment, a lotion, a crème, a bath admixture, a gel, a paste, a milk, a suspension, an aerosol, a spray, a film, a foam, a serum, a swab, a pledget, a pad, a patch, a powder, a paste, a liniment, viscous emulsion, or another formulation which is appropriate for topical administration.

Such compositions for topical administration (including ophthalmic compositions) may further include physiologically acceptable components such as carriers, surfactants, preservatives, stabilizing agents, buffers, excipients and emulsifiers suited for this type of administration. Suitable components for topical delivery systems are preferably chosen from components that do not cause excessive or unavoidable irritation or pain to the recipient. Carriers include diluents and provide the medium in which the pharmaceutical constituents are dissolved, dispersed or distributed. Formulations include those formulated in PBS, water or saline or any other pharmaceutically acceptable liquid.

The composition according to the invention may comprise, but are not restricted, a carrier such as an aqueous liquid base, nonaqueous liquid base, water soluble gel, a mineral oil base, emulsion, ointment, crème, gel or lotion, suspension of solid particles in a liquid.

The topical availability of active ingredients depends on two contrasting factors: their ability to dissolve in the carrier (gel, creme-hydrophilic), and their ability to permeate the skin barrier (ie, the stratum corneum-hydrophobic), thus requiring a unique hydrophobic-hydrophilic balance. Formulations require addition of excipients, such as permeation enhancers and solubilizers to facilitate either or both of the transport processes (dissolution into vehicle and diffusion across skin). Additives, such as alcohols, fatty alcohols, fatty acids, mono- di- or tri-glycerides, glycerol monoethers, cyclodextrin and derivatives, polymers, bioadhesives, terpenes, chelating agents and surfactants have been disclosed to increase transdermal delivery of drugs. It is within the present invention to make use of such excipients.

Any method, not limited to the above-mentioned, for increasing transdermal delivery is within the scope of the present invention. The therapeutic composition according to the present invention may therefore comprise surfactants such as ionic and/or non-ionic surfactants. Suitable non-ionic surfactants include for example: fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols); polypropylene glycol ethoxylates (Pluronic); fatty acid alkylolamides (fatty acid amide polyethylene glycols); alkyl polyglycosides, N-alkyl-, N-alkoxypolyhydroxy fatty acid amide, in particular N-methyl-fatty acid glucamide, Poloxamer 188, sucrose esters; sorbitol esters, esters of sorbitol polyglycol ethers and lecithin. Ionic surfactants include for example sodium lauryl sulfate, sodium laurate, polyoxyethylene-20-cetylether, Laureth-9, sodium dodecylsulfate (SDS) and dioctyl sodium sulfosuccinate.

Alcohols include, but are not limited to, ethanol, 2-propanol and polyols such as polyethylene glycol (PEG), propylene glycol, glycerol, propanediol.

Methods for enhancing drug delivery through topical administration may be applied with the present invention, and include any means of increasing absorption, minimizing metabolism, and/or prolonging the half-life of the active ingredient of the composition, such as flavonoid. Such means include the use of transporters of the type liposomes, ISCOMs, nano-particles, microspheres, hydrogels, organogels, polymers or other micro-encapsulation techniques.

Bioadhesives within the scope of the present invention for use in topical delivery include adhesives of the skin and mucous tissue such as mucin binding and/or epithelial tissue binding polymers.

In embodiments of the invention wherein the composition is formulated as a gel or gel-like substance, cream or viscous emulsion it is preferred that said composition comprises at least one gelling component, polymer or other suitable agent to enhance the viscosity of the composition. Any gelling component known to a person skilled in the art, which has no detrimental effect on the area being treated, and is applicable in the formulation of compositions and pharmaceutical compositions for topical administration to the skin, eye or mucous can be used. For example, the gelling component may be selected from the group of: acrylic acids, carbomer, carboxypolymethylene, such materials sold by B.F. Goodrich under the trademark Carbopol (e.g. Carbopol 940), polyethylene-polypropyleneglycols, such materials sold by BASF under the trademark Poloxamer (e.g. Poloxamer 188), a cellulose derivative, for example hydroxypropyl cellulose, hydroxyethyl cellulose, hydroxyethylene cellulose, methyl cellulose, carboxymethyl cellulose, alginic acid-propylene glycol ester, polyvinylpyrrolidone, veegum (magnesium aluminum silicate), Pemulen, Simulgel (such as Simulgel 600, Simulgel EG, and simulgel NS), Capigel, Colafax, plasdones and the like and mixtures thereof.

A gel or gel-like substance according to the present invention comprises for example less than 10% w/w water, for example less than 20% w/w water, for example at least 20% w/w water, such as at least 30% w/w water, for example at least 40% w/w water, such as at least 50% w/w water, for example at least 75% w/w water, such as at least 90% w/w water, for example at least 95% w/w water. Preferably said water is deionised water.

In one embodiment the composition is formulated as an ointment. Any ointment components known to a person skilled in the art, which has no detrimental effect on the area being treated, and is applicable in the formulation of compositions and pharmaceutical compositions for topical administration to the skin, eye or mucous can be used. For example, one carrier may be a petrolatum carrier.

In one embodiment the composition is formulated so it is a liquid comprising a least one flavonoid and at least one indole in solution or in suspension. The composition may be formulated in the any liquid form suitable for topical application such as eye-drops, artificial tears, eye washes, or contact lens adsorbents comprising a liquid carrier such as a cellulose ether (e.g. methylcellulose).

The liquid may be any useful liquid, however it is frequently preferred that the liquid is an aqueous liquid. It is furthermore preferred that the liquid is sterile. Sterility may be conferred by any conventional method, for example filtration, irradiation or heating.

The liquid may comprise one or more lipophile vehicles, for example one or more lipophile vehicle suitable for controlled release of flavonoids and/or the indole and/or the synthetic heterodimer.

Another preferred embodiment of the present invention is to provide a composition formulated for oral administration in the form of a dietary supplement, nutraceutical composition, medical food, or animal feed. In particular embodiments, said oral administration prevents, treats or ameliorates the symptoms of a disease or disorder of the eye and adnexa of the eye (including eyelids and lacrimal apparatus of the eye), particularly associated with surface inflammation of the eye and/or tear ducts. Embodiments of the compositions of the present invention are intended for administration to a mammal, in particular a human being, in a suitable dosage form as is known in the art. Among oral dosage forms, solid and liquid dosage forms are particularly preferred.

Oral solid dosage forms are well known in the art and include tablets, caplets, gelcaps, capsules, and edible food items. Oral solid dosage forms can be made with one or more pharmaceutically acceptable excipients. Pharmaceutically acceptable excipients assist or make possible the formation of a dosage form for a bioactive material and include diluents, binding agents, lubricants, glidants, disintergrants, coloring agents, and flavorants and nutrients. An excipient is pharmaceutically acceptable if, in addition to performing its desired function, it is non-toxic, well tolerated upon ingestion, and does not interfere with absorption of bioactive materials.

Tablets can be made by well-known compression techniques using wet, dry, or fluidized bed granulation methods. The ingredients are mixed in a blender. Useful blenders include the twin-shell type, the planetary mixer type, and the high-speed high-shear type; all of which are known to the skilled artisan. The blended combination is sieved and dried to a granulate. The granulate is then compressed into tablets using a tableting press as is known in the art. Preferably, the granulate is sieved before the compression to make sure that the granulate has the desired particle size. Tablets can be either coated or uncoated as is known in the art.

The proportion of components and constituents, binder, excipients, and water (if used), as well as the time and intensity of mixing, will be optimized by the routiner to obtain a granulate with the desired tableting characteristics.

Capsules, also known as dry filled capsules, are oral solid dosage forms in which the composition is contained in a swallowable container of suitable size, typically made of gelatin. Hard empty capsules suitable for containing the composition of the present invention are available from several sources, for example, Tishcon Gel-Tec, 2410 N. Zion Rd., Salisbury, Md. 21801; the capsules are supplied in two halves and in various sizes. The sizes are typically designated by number; 000 is presently the largest size in common use, 5 is the smallest size presently in common use. The capsule halves can be colored by a suitable coloring agent and each halve can be the same or a different color.

In making a solid oral dosage form that is a capsule, the components and constituents are combined and mixed together, with or without a diluent such as lactose, mannitol, calcium carbonate, or the like using any of the mixers described above. Prior to mixing, a granulate of one or more of the components or constituents can be prepared as in the making of tablets. The combined mixed components, constituents and excipients, if any, are packed into one capsule half. The filled half-capsule is then closed with the other capsule half. Manual, semiautomatic, and automatic equipment for filling capsules are known in the art.

The oral solid dosage form used in the present invention can be a chewable food item that includes the nutraceutical composition. In addition to the nutraceutical composition, the chewable food item can and preferably does contain one or more nutrients such as soy protein isolate, soy protein hydrolysate, calcium caseinate, whey protein isolate, whey protein concentrate, milk protein isolate, skim milk powder, yogurt solids, or hydrolyzed bovine gelatin in combination with oils, binders, fillers, and processing aids known in the art. The oral solid dosage form is formed of a mass having the desired ingredients into a shape, preferably a bar having a circular, semicircular, or rectangular cross-section by, for example, extrusion, and cut into chewable food item dosage forms of about 50 to about 175 grams each whereby each such dosage form includes a blood sugar and glycosylation maintaining effective amount of the nutraceutical composition.

Oral liquid dosage forms may be hybrid. In one example of an oral liquid dosage form that is a hybrid, one or more constituents or components, or a fraction of them, are dissolved in a vehicle, and the remainder are in suspension in the vehicle. In another example of a liquid oral composition that is a hybrid, one or more constituents or components, or any fraction thereof, of the nutraceutical composition are dissolved in a first vehicle and the remainder are suspended or dissolved in a second vehicle that forms an emulsion with the first vehicle. Other hybrid liquid oral dosage forms will be apparent to the skilled artisan and are within the scope of this invention.

Methods of Treating

The methods of the present invention provide for methods of treating, preventing, ameliorating symptoms of, reducing inflammation associated with, etc. of diseases or disorders associated with ocular surface inflammation, or inflammation of the adnexa of the eye in a patient, preferably a human patient, suffering therefrom by administration of a therapeutically effective amount of a composition of the invention comprising an indole and a flavonoid as an admixture and/or a heterodimer thereof as described above. In specific embodiments, the methods of the invention encompass treating, preventing or ameliorating one or more symptoms in a patient, preferably a human patient, of dry eye symptoms associated with dry eye disease or Sjögren's syndrome by administration of a therapeutically effective amount of a composition of the invention comprising an indole and a flavonoid, either as a mixture or as a heterodimer or as a combination of two separate compositions containing the indole and the flavonoid individually. In methods of the invention, administration of the composition of the invention ameliorates or reduces one or more symptoms of an ocular disorder, such as ocular, dryness, irritation, foreign body sensation, light sensitivity, and itching. In certain embodiments, the invention encompasses veterinary use of the compositions and methods of the inventions, for example, to treat, prevent or reduce the symptoms of an ocular disease or disorder in non-human animals, such as, companion animals, such as dogs, cats, etc., livestock, such as cattle, pigs, sheep, horses, goats, bison, etc.

The ophthalmic compositions according to the present invention may be administrated once or more than once a day, for example they may be administered in the range of 2 to 10 times a day, such as 2 to 7 times, for example 2 to 5 times, such as 2 to 4 times, such as 2 to 3 times a day. In a preferred embodiment of the invention the composition is administered twice a day. In another preferred embodiment of the invention the composition is administered once a day.

The oral compositions according to the present invention may be administrated once or more than once a day, for example they may be administered in the range of 2 to 10 times a day, such as 2 to 7 times, for example 2 to 5 times, such as 2 to 4 times, such as 2 to 3 times a day. In a preferred embodiment of the invention the composition is administered twice a day. In another preferred embodiment of the invention the composition is administered once a day.

The treatment period may vary depending on the specific disease or condition treated. The compositions according to the present invention may be administrated to the subject for a period of treatment of one or more than one week such as two weeks, three weeks, four weeks, five weeks, six weeks, seven weeks, eight weeks or more than eight weeks. The treatment may be repeated on subjects, who relapse.

However, typically the treatment period is for at least 2 weeks, such as e.g., at least 3 weeks, at least 4 weeks, at least 5 weeks, 6 weeks, 7 weeks, 8 weeks or more than eight weeks. In a preferred embodiment of the invention subjects in need of treatment are treated with a composition according to the invention for a period of about 3-6 weeks, this treatment may optionally be combined with the use of an eye cleaner as described above. In a more preferred embodiment of the invention the composition according to the invention is applied for a period of about 3 weeks.

EXAMPLES

Herein we describe the synthesis of a new heterodimer formed by conjugation of an indole as described above, such as indirubin-3'-oxime (I3O), and a flavanoid as described above, such as quercetin or baicalein and the method for synthesis of this new heterodimer is described below. It will be apparent to those of ordinary skill in the art upon review of the disclosed example that various alternative methods are available for synthesizing the heterodimers of the invention.

The effect of the combination of quercetin and indirubin-3'-oxime (I3O) and the combination of baicalein and I3O, is determined by in vitro assays and, for the combination of quercetin and I3O, evaluation of the suppression of the immune response in the eye when applied topically as a form of eye drops as evidenced by the experiments detailed below. It will be apparent to those of ordinary skill in the art that various alternative methods are available for assessing the efficacy of the inventive compositions.

Example 1

Synthesis of Heterodimer a and Heterodimer B

Synthesis of Heterodimer A and Heterodimer B formed by the reaction of quercetin and indirubin-3'-oxime (I3O). Quercetin and 4-bromo-butyric acid are dissolved in a 1:1.2 molar ratio in dry DMF. $K_2CO_3$ and NaI are added into the solution which is then heated under $N_2$ atmosphere to 95° C. for 2 hours while stirring. The reaction mixture is poured into water (50 mL) and the organic materials are extracted into ethyl acetate (3×20 mL). This extract is washed with $H_2O$ (5 mL), dried and the solvent removed by evaporation in vacuum. The residue is purified by column chromatography on silica gel using hexane-acetone to elute the desired protected flavone.

The intermediate, i.e, the protected flavone, and I3O (approximately 1:1) are dissolved in dry THF. 1.2 equivalents of EDC HCl is added and the resulting solution is stirred overnight. After the reaction, THF is removed under vacuum and the residue is worked up by extraction with ethyl acetate and water. The organic layer is dried and then evaporated in vacuum. The resulting residue is purified by column chromatography on silica gel using hexane-acetone to isolate Heterodimer A and Heterodimer B separately.

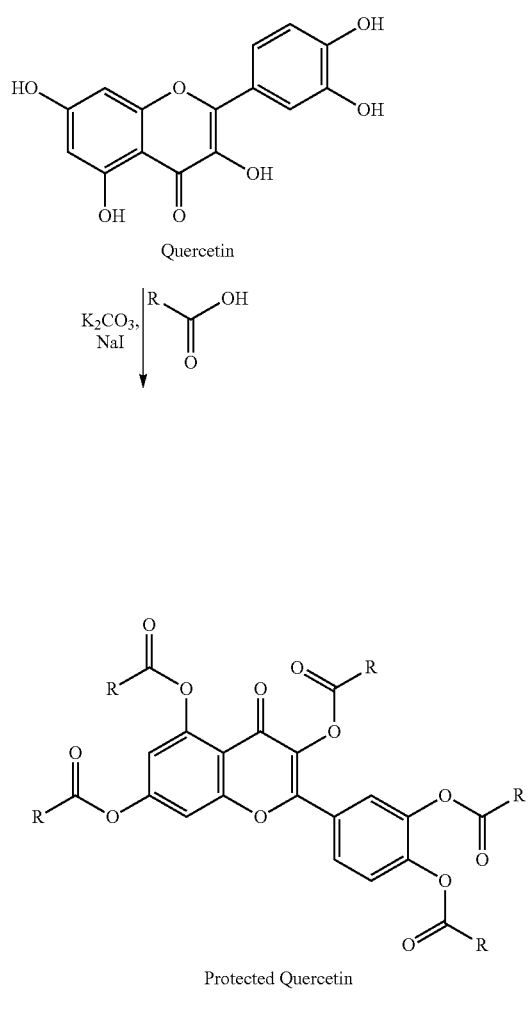

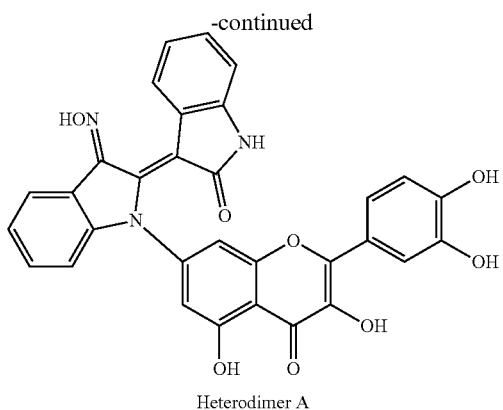

Heterodimer A and

Heterodimer B

Example 2

Effect of Indirubin-3'-Oxime and Quercetin on Cultured Goblet Cells

Materials and Methods

Indirubin-3'-oxime (I3O) is obtained from Sigma-Aldrich (USA) and quercetin is obtained from National Institute for the Control of Pharmaceutical and Biological Products (China). I3O and quercetin are dissolved in DMSO to form a stock solution with the concentration of 10 mM and 30 mM respectively. All the stock solutions are stored at $-20°$ C.

Isolation and Culture of Goblet Cells. An organ culture of mouse conjunctiva was used to obtain goblet cells. Goblet cells were the primary cells migrated out from the explants. Conjunctival tissues were dissected and placed in Phosphate buffered saline (Gibco, Thermo Fisher Scientific, Waltham, Mass.). Each conjunctival tissue was dissected into 12 to 16 pieces and were settled on a 12-well culture plate contained just enough medium to cover the bottom of the well. RPMI-1640 medium (Thermo Fisher Scientific, Waltham, Mass.) supplemented with 10% fetal bovine serum, 1 mM sodium pyruvate, 10 mM HEPES, 100 μg/ml gentamycin, and 1× non-essential amino-acid mixture (Thermo Fisher Scientific, Waltham, Mass.) was used to feed the explants. Fifty microliters of the complete RPMI was applied to the explant culture every day for the first 4 days and then feed the culture with 500 μl complete RPMI every two days. The explants were grown for 14 days; and then the goblet cells were trypsinized and transferred to 24-well culture plates.

Propidium Iodide Staining to Assess Cell Viability: The culture was treated with 2 μg/ml propidium iodide (PI) (Invitrogen, Thermo Fisher Scientific, Waltham, Mass.), which only stained dead cells. Then the culture was exposed to 1 μg/ml DAPI (Invitrogen, Thermo Fisher Scientific,

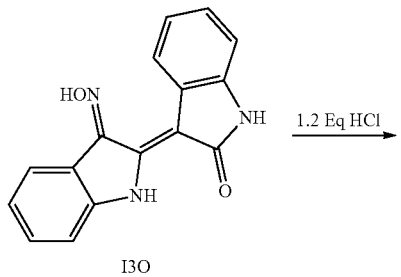

Waltham, Mass.), which stained the nuclei of both live and dead cells. Five fields of each condition in each culture were imaged and the percentage of live cells ({number of DAPI nuclei−number of PI nuclei}/number of DAPI nuceli) was calculated.

MUC5AC ELISA: Mucin secretion was a normal function for the goblet cells. Mucin-5 Subtype AC (MUC5AC) ELISA kit was purchased from Biotang (Waltham, Mass.) and the amount of the mucin in supernatant was measured according to the manufacturer's instructions. The goblet cells were lysed and the amount of protein was measured using the BCA Protein Assay Kit (Pierce, Rockford, Ill.). The protein measured was used to normalize the mucin secretion in the supernatant and was presented as MUC5AC ng/mg of cellular protein.

Effect on Goblet Cell Function

Figure 3:
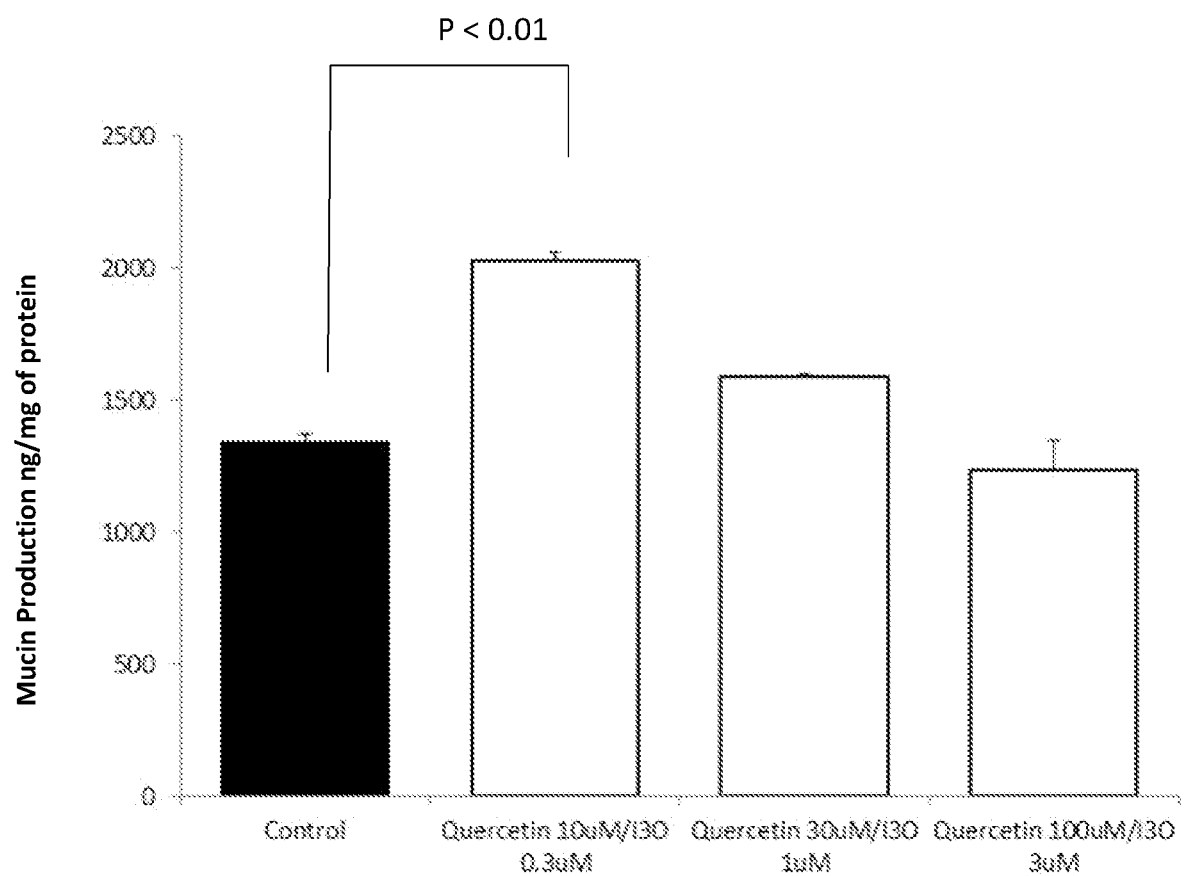
FIG. 3 shows the results of an in vitro investigation of the effect on mucin production of cultured goblet cells with different concentrations of a combination of Quercetin/and I3O. Quer/I3O Low: 10 μM Quercetin and 0.3 μM I3O; Quer/I3O Medium: 30 μM Quercetin and 1 μM I3O; Quer/I3O High: 100 μM Quercetin and 3 μM I3O.

To evaluate the effect of the agents on normal goblet cell functions, goblet cells were grown to 85% confluency. Prior to any exposure to the agents, cells were maintained for 24 hours in serum-free medium. After this, cultured conjunctival goblet cells were treated with the following formulations for 24 hours: 10 μM Quercetin/0.3 μM I3O (low); 30 μM Quercetin/1 μM I3O (medium); 100 μM Quercetin/3 μM I3O (high). Control cells were not treated. Cells were tested for mucin production. FIG. 3 shows that the lowest concentration of the Quercetin/I3O combination, 10 μM Quercetin/0.3 μM I3O, enhanced mucin production in the cultured goblet cells.

To evaluate the effect of the agents on inflamed goblet cells, goblet cells were grown to 85% confluency. Prior to any exposure to the agents, cells were maintained for 24 hours in serum-free medium. After this, cultured conjunctival goblet cells were incubated for 24 hours with agents as follows: untreated control; 10 ng/ml TNFα; 10 ng/ml TNFα with 30 μM Quercetin and 1 μM I3O; and 10 ng/ml TNFα with 30 μM baicalein and 1 μM I3O. Cells were tested for viability and mucin production. The TNFα induces inflammation in the cultured cells.

Figure 4A:
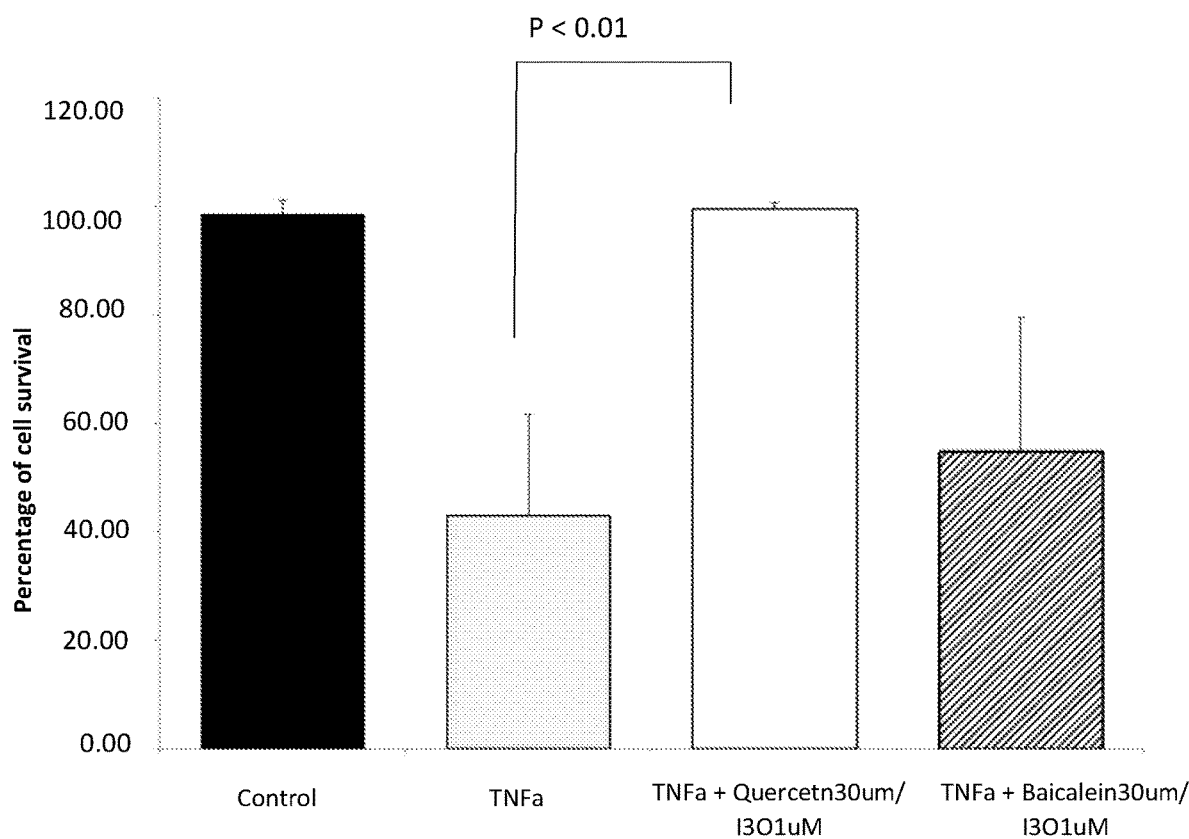
FIGS. 4A and 4B show the effect of the 30 μM Quercetin/1 μM I3O and the 30 μM baicalein/1 μM I3O combinations on (A) survival of cultured goblet cells and (B) mucin production in cultured goblet cells treated with TNFα simultaneously with the quercetin and I3O or baicalein and I3O as compared to control cells treated only with TNFα.
Figure 4B:
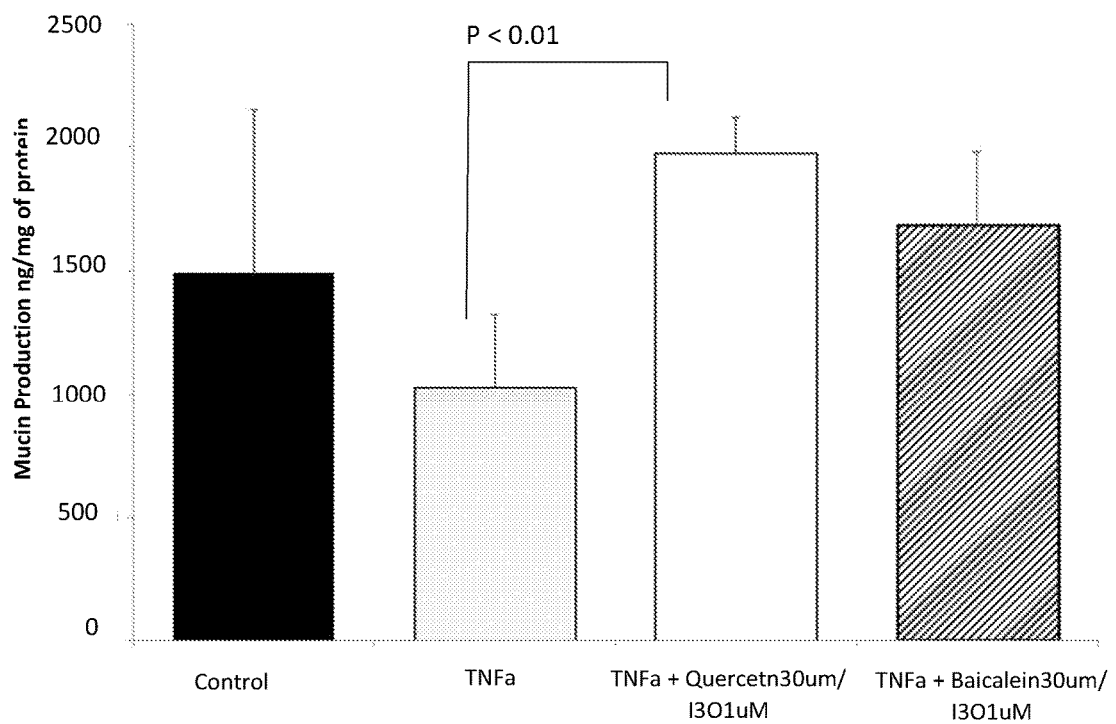

FIG. 4A shows that 30 μM Quercetin/0.5 μM I3O increased the survival of goblet cells to the level of control. 30 μM Baicalein/0.5 μM I3O was not able to increase the survival of goblet cells (t-test vs control: P<0.01). This demonstrated only the combination of 30 μM Quercetin/0.5 μM I3O was able to counteract the apoptotic effect of TNFα and to increase the survival of the goblet cells. FIG. 4B shows that 30 μM Quercetin/1 μM I3O and 30 μM baicalein/1 μM I3O increased mucin production in goblet cells treated with TNFα to approximately the level of the control (with the 30 μM Quercetin/1 μM I3O increasing mucins production with P<0.01), demonstrating that the combination counteracted the effect of TNFα and restored the mucin production to normal from the TNFα treatment.

Example 3

Effect of Indirubin-3'-oxime and Quercetin in Murine Model of Sjögren's Syndrome Sjögren's disease is associated with increased levels of Th1 inflammatory effectors known to produce cytokines like IFN-γ and TNF-α as well as Th17 effectors associated with chronic inflammation and characterized by expression of IL-17A and IL-6 in the periphery and exocrine glands (Nguyen et al., 2008, Arthritis Rheum 58: 734-743; van Woerkom et al., 2005, Ann Rheum Dis 64: 1474-1479). The ocular component of the disease has been described to involve infiltration of ocular surface and related tissues by inflammatory effectors that produce both Th1 and Th17 cytokines (Nguyen & Peck, 2009, Ocul Surf 7: 11-27; Stern et al., 2005, Invest Ophthalmol Vis Sci 43: 2609-2614; Pflugfelder et al., 1999, Curr Eye Res 19: 201-211). Thrombospdondin-1 deficient (TSP-1null) mice develop chronic and progressive ocular disease as seen in Sjögren's patients (Turpie et al., 2009, Am J Pathol 175: 1136-1147; Contreras-Ruiz et al., 2013, PLoS One 8: e75937) and exhibit these changes in cytokine levels as well. The clinical signs, pathology and disease development in this mouse model very closely resemble that seen in human patients making it an ideal pre-clinical model to test therapeutic efficacy of potential drugs that can reduce ocular inflammation.

The disease onset with ocular surface damage in TSP-1null mice is detected by 12 weeks of age when significant disruption of corneal barrier integrity and increased expression of inflammatory cytokines IFN-γ, TNF-α, IL-17A, and IL-6 is detected in the conjunctiva (Pflugfelder et al., 1999). The secretory function of lacrimal gland in these mice is abnormal resulting in reduced secretion of antimicrobial enzymes like peroxidase (Turpie et al., 2009).

Materials and Methods

Mice. Thrombospondin (TSP)-1 null mice (C57BL/6 background), were bred in-house in a pathogen-free facility at Boston University School of Medicine, Boston, Mass. All experiments were conducted in accordance with institutional guidelines and ARVO Statement of the Use of Animals in Ophthalmic and Vision Research.

Corneal Fluorescein Staining. Sodium fluorescein (1%), 1 μl was applied to the cornea of mice under anesthesia. Three minutes later, eyes were flushed with PBS to remove excess fluorescein, and corneal staining was evaluated and photographed with a slit lamp biomicroscope (Humphrey-Zeiss, Dublin, Calif.) using a cobalt blue light. Punctate staining was recorded using a standardized National Eye Institute grading system of 0 to 3 for each of the five areas of the cornea (Lemp, 1995, CLAO J. 21:221-232).

Inflammatory Cells in Treated Conjunctiva: The whole eye including the eye lids was embedded in paraffin and sectioned in 5 μM in thickness. After deparaffin, the section was labeled with rat anti-CD45 IgG (BD Biosciences, San Jose, Calif.). Then the ABC kit of alkaline phosphatase (Vector Labs, Burlingame, Calif.) and Vector Red (Vector Labs, Burlingame, Calif.) were used. The number of CD45 cells was counted using an epi-fluorescence microscope.

Real-Time PCR. Total RNA was isolated from the conjunctiva tissues harvested from WT or TSP-1 null mice (n=4 to 5) using RNA STAT-60 kit (Tel-Test, Inc., Friendswood, Tex.) according to the manufacturer's instructions. cDNA was synthesized by reverse transcribing RNA using oligo dT and M-MLV RT (Promega, Madison, Wis.). SYBR green real-time PCR assay is used to determine relative quantitative expression of inflammatory cytokines interferon gamma (IFN-γ), tumor necrosis factor alpha (TNF-α), interleukin 6 (IL-6) or interleukin 17A (IL-17A). Sequences of the Forward (F) and Reverse (R) primers for use with these genes were as follows:

```
IFN-γ
                                    (SEQ ID NO: 1)
    F   5'-TCAGCAACAACATAAGCGTCAT-3'

(SEQ ID NO: 2)
    R   5'-GACCTCAAACTTGGCAATACTCAT-3'
```

```
TNF-α
                                                  (SEQ ID NO: 3)
F      GGCCTCCCTCTCATCAGTTCTATG-3'

(SEQ ID NO: 4)
R      5'-GTTTGCTACGACGTGGGC TACA-3'

IL-6
                                                  (SEQ ID NO: 5)
F      5'-AGTCAATTCCAGAAACCGCTATGA-3'

(SEQ ID NO: 6)
R      5'-TAGGGAAGGCCGTGGTTGT-3'

IL-17A
                                                  (SEQ ID NO: 7)
F      5'-AGTGAAGGCAGCAGCGATCAT-3'

(SEQ ID NO: 8)
R      5'-CGCCAAGGGAGTTAAAG-3' glyceraldehyde-3-phosphate dehydrogenase
                                                  (SEQ ID NO: 9)
F      5'-CGAGAATGGGAAGCTTGTCA-3'

(SEQ ID NO: 10)
R      5'-AGACACCAGTAGACTCCACGACAT-3'
```

Amplification reactions were set up using SurePRIME-&GO mastermix (MP Biomedicals, Solon, Ohio) in triplicates with the thermal profile: 50° C. for 2 minutes; 1 cycle, 95° C. for 15 minutes; 1 cycle, 52° C. to 55° C. for 1 minute, 40 cycles, 72° C. for 30 seconds; 1 cycle on ABI Prism analyzer (Applied Biosystems Inc., Foster City, Calif.). Fluorescence signal generated at each cycle was analyzed using system software. The threshold cycle values were used to determine relative quantitation of gene expression with glyceraldehyde-3-phosphate dehydrogenase as a reference gene.

Effect in Murine Model of Sjögren's Syndrome

TSP-1 deficient (null) mice (12 wk old) were treated with eyedrops twice daily for a period of two weeks. The 5 μL eye drops were either PBS as a control or 0.5 μM I3O and 30 μM quercetin in PBS, 0.5 μM I3O alone in PBS, or 30 μM quercetin alone in PBS. An eyedrop was topically applied to the eyes of the unanesthetized mice. Age matched untreated wild type mice received placebo eyedrops of PBS alone. Clinical signs of dry eye disease, including effect on the corneal surface and peroxidase levels in tears, were measured at baseline (prior to initiating treatment) and at the end of week 1 and effect on the corneal surface was assayed again at the end of week 2. Mice were then euthanized at the end of the study period for further studies. The conjunctiva of the left eye of each animal was dissected for real time PCR and eyes were fixed for histology, in particular to analyse the presence of CD45+ cells in conjunctiva of the eyes.

Figure 5A:
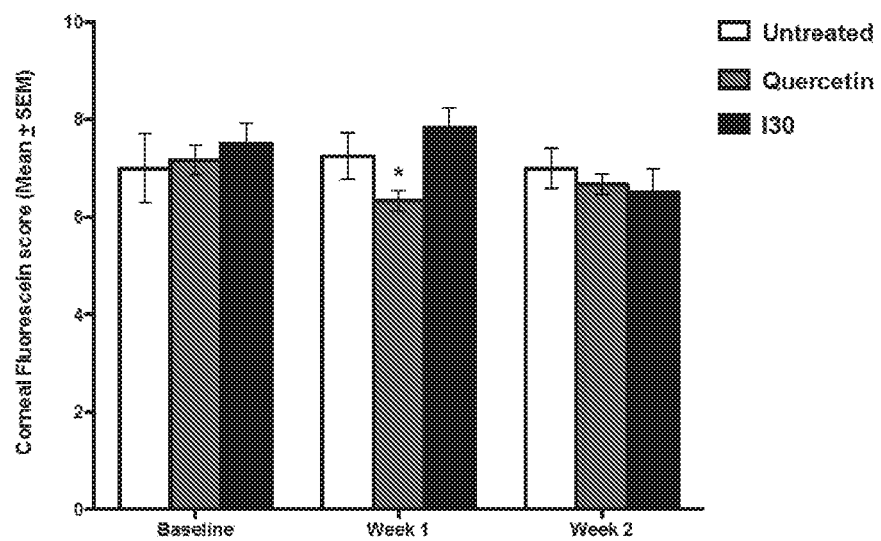
FIGS. 5A and 5B present the effect of twice a day administration of eye drops for two weeks on the corneal surface in a murine model of Sjogren's syndrome as determined by corneal fluorescein staining at week 1 and week 2 as compared to the corneal surface of control mice. A: results of twice a day administration of 30 μM Quercetin or 0.5 μM I3O (each as a 5 μl drop) individually. B: results of twice a day administration of a combination of 30 μM Quercetin and 0.5 μM I3O (as a 5 μl drop).
Figure 5B:
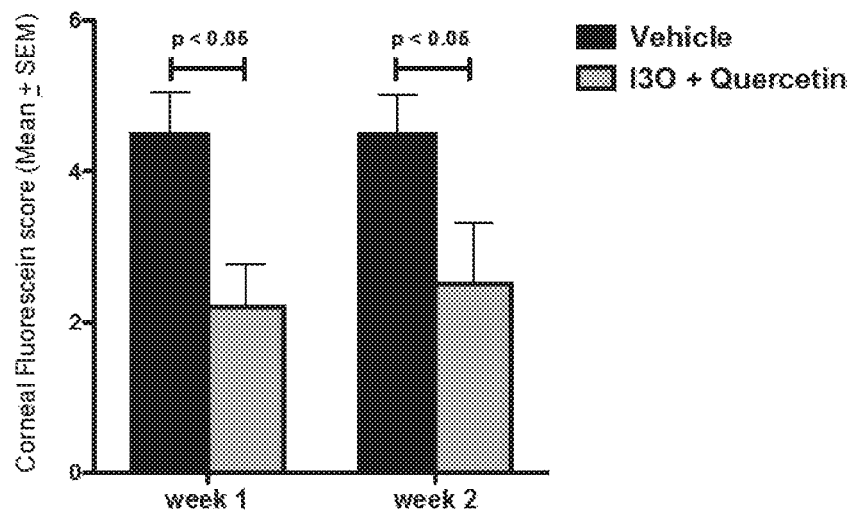
Figure 6:
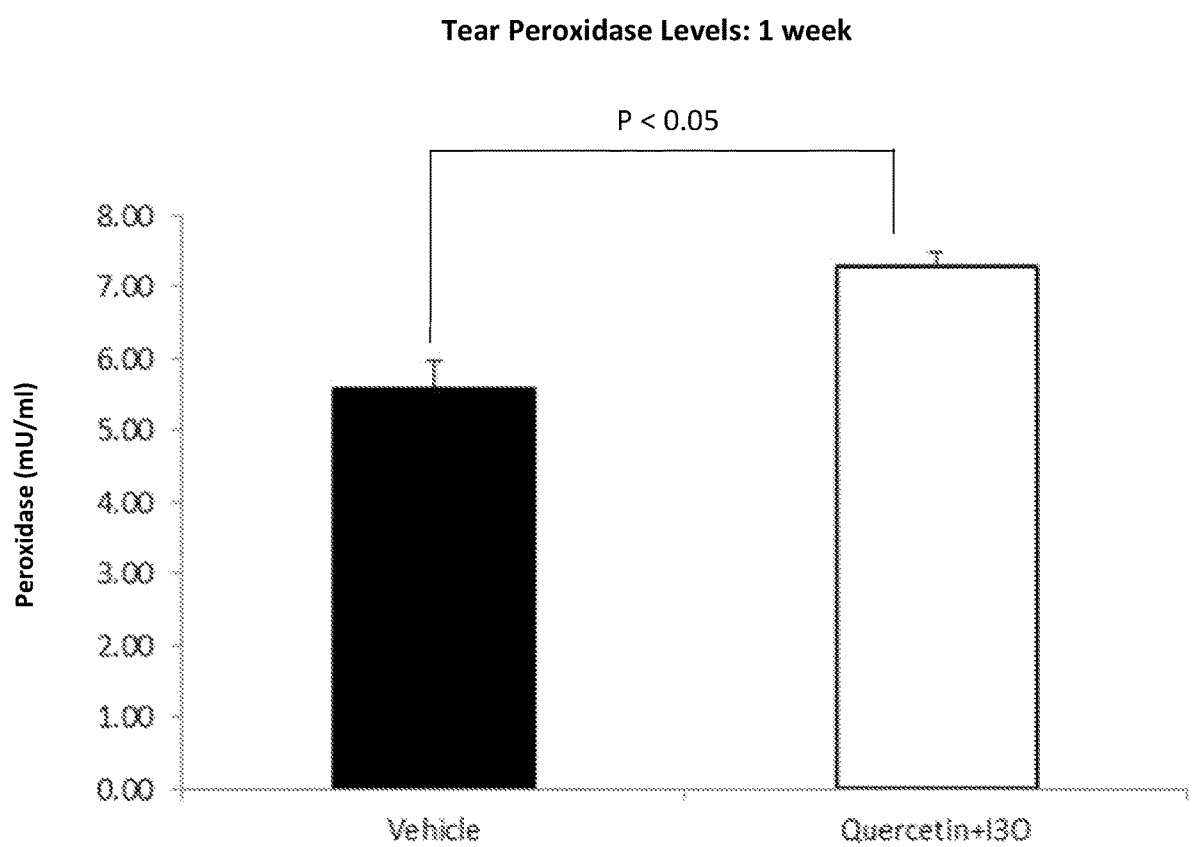
FIG. 6 shows the effect of twice a day administration of eye drops containing 30 μM Quercetin and 0.5 μM I3O or a control for 1 week on the level of peroxidase in tears.

As shown in FIG. 5A, treatment with quercetin alone elicited significant improvement in the corneal surface, as evidenced by a reduction in the corneal fluorescein score, at week 1. Treatment with I3O alone showed a small improvement in corneal fluorescein score at week 2, but it was not significant. However, FIG. 5B shows that the combination of 0.5 μM I3O and 30 μM quercetin significantly reduced the corneal damage (showed by corneal fluorescein staining at both week 1 and week 2). At week 1, as shown in FIG. 6, treatment with the combination of quercetin and I3O increased tear peroxidase levels as compared to control, suggesting treatment with the combination improved secretory function of the lacrimal gland.

Figure 7:
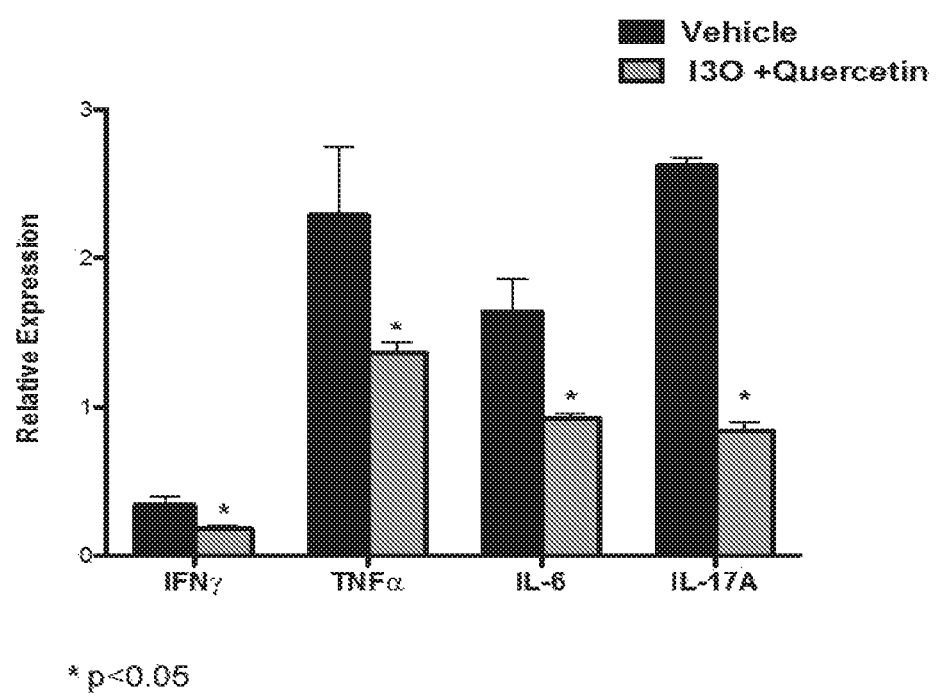
FIG. 7 shows the effect on the expression of inflammatory cytokines, as assessed by quantitative PCR, in the conjunctiva of murine model of Sjögren's syndrome of administration of the combination of 30 μM Quercetin and 0.5 μM I3O (as a 5 μl drop) twice a day for two weeks.

In the mice treated with the combination of 30 μM Quercetin and 0.5 μM I3O, their conjunctiva showed a significantly reduced expression of inflammatory cytokines IFNγ, TNFα, IL-6 and IL17A as assessed by real time PCR as shown in FIG. 7, indicating a reduction in inflammation.

Figure 8:
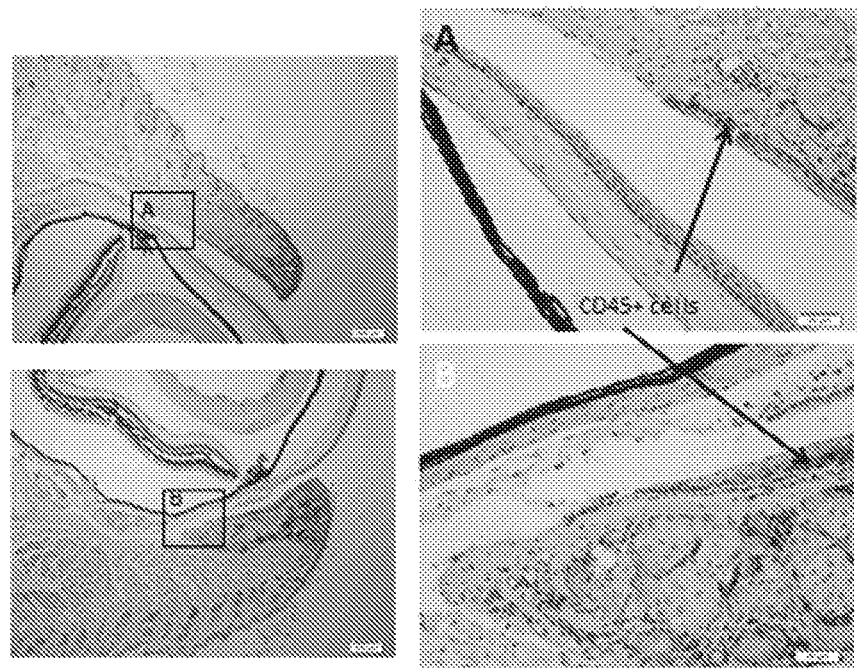
FIG. 8 presents histology of an eye of a TSP-1 null mouse treated with vehicle only and labeled to detect CD45+ cells in the conjunctiva.
Figure 9:
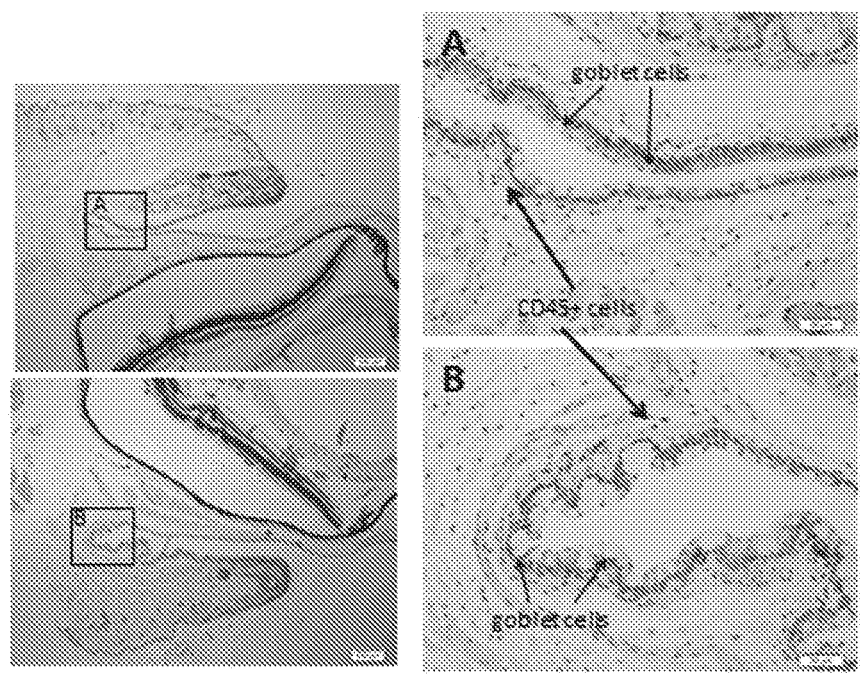
FIG. 9 presents histology of an eye of a TSP-1 null mouse treated twice a day for two weeks with eyedrops containing 30 μM Quercetin and 0.5 μM I3O and labeled to detect CD45+ cells in the conjunctiva.
Figure 10:
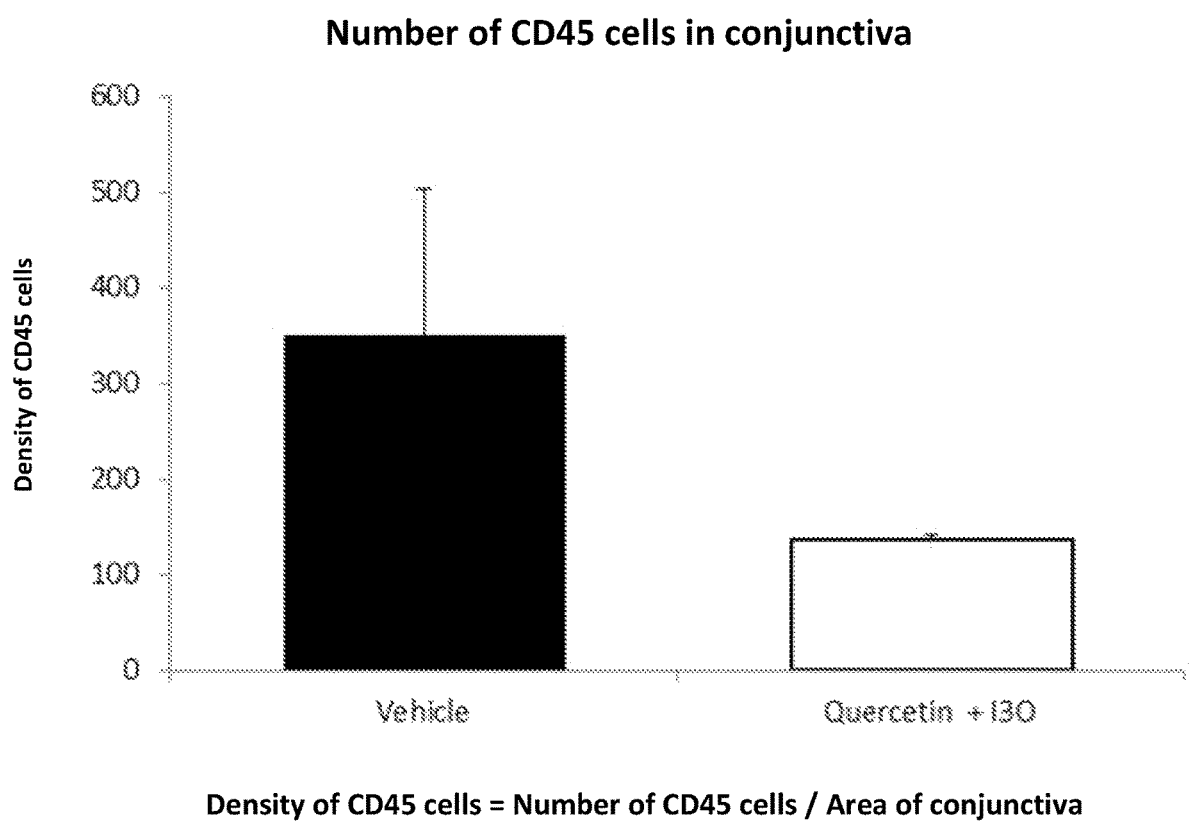
FIG. 10 shows the effect on inhibiting the inflammatory cells infiltration into the conjunctiva as assessed by immunohistochemistry. The TSP-1 deficient mice were treated with the combination of 30 mM Quercetin and 0.5 μM I3O (as a 5 μl drop) twice a day for two weeks.

Histology on the eyes of the TSP-1 null mice treated with the combination of 30 μM Quercetin and 0.5 μM I3O or vehicle control demonstrated a reduction in the density of CD45+ cells in the conjunctiva of the treated eye. Representative sections of eye stained for CD45+ either treated with control vehicle or the quercetin/I3O combination are shown in FIG. 8 and FIG. 9, respectively. The density of the CD45+ cells in the conjunctiva was also determined, with a reduction in the density of CD45+ cells in the conjunctiva of mice treated with the quercetin-I3O combination as compared to control, see FIG. 10.

We claim:

1. A method for treating an ocular disease in a patient, wherein the ocular disease is characterized by inflammation of the eye or adnexa of the eye, comprising administering to the patient suffering therefrom a composition comprising a therapeutically effective amount of a combination of a compound of Formula 3:

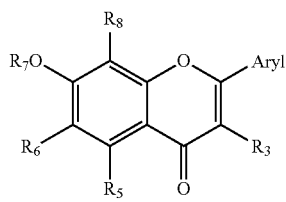

Formula 3 wherein:
Aryl is phenyl, optionally substituted by one or more substituents selected from the group consisting of OH and $OC_{1-3}$ alkyl;
$R_3$ is H, OH, $OCH_3$ or OP;
$R_5$ is H, OH, $OCH_3$ or OP;
$R_6$ is H, OH, $OCH_3$ or OP;
$R_7$ is H or P;
$R_8$ is H, OH, $OCH_3$ or OP; and
P is a protecting group selected from the group consisting of $C(O)C(CH_3)_3$, C(O)-phenyl, $C(O)CH_3$ and $C(O)CH_2Cl$; and
a compound of Formula 1:

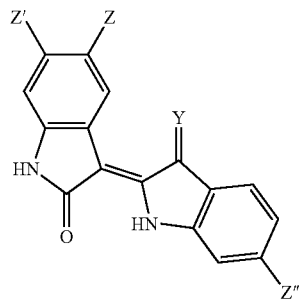

Formula 1 wherein:
Y is NH or NOH;
Z is H, Cl, Br or I;
Z' is H, Cl, Br or I; and
Z" is H, Cl, Br or I; or
a compound of Formula 2:

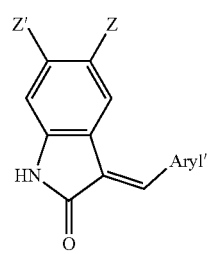

Formula 2 wherein:
Aryl' is phenyl, optionally substituted by one or more substituents selected from the group consisting of F, Cl, Br, I, OH, $NH_2$, $C_{1-3}$ alkyl, $C(O)_2C_{1-3}$alkyl, C(O)NH($C_{1-3}$ alkyl), $C(O)N(C_{1-3}$ alkyl$)_2$, $NH(C_{1-3}$ alkyl), $N(C_{1-3}$ alkyl$)_2$, NH(aryl), N(aryl)$_2$ and $S(O)_2(C_{1-3}$ alkyl);
Y is NH or NOH;
Z is H, Cl, Br or I; and
Z' is H, Cl, Br or I.

2. The method according to claim 1, wherein the ocular disease is selected from the group consisting of dry eye disease and Sjögrens disease.

3. The method according to claim 1, wherein the composition comprises a therapeutically effective amount of a combination of a compound of Formula 3 and a compound of Formula 1.

4. The method according to claim 1, wherein the composition comprises from 0.1 ng/mL to 100 mg/mL of the compound of Formula 3 and from 0.1 ng/mL to 100 mg/mL of the compound of Formula 1 or Formula 2.

5. The method according to claim 1, wherein the composition comprises the compound of Formula 3 and the compound of Formula 1 or Formula 2 in a molar ration from 1:1000 to 1000:1.

6. The method according to claim 1, wherein the composition is formulated as an ophthalmic composition.

7. The method according to claim 1, wherein the compound of Formula 1 or Formula 2 is selected from the group consisting of:

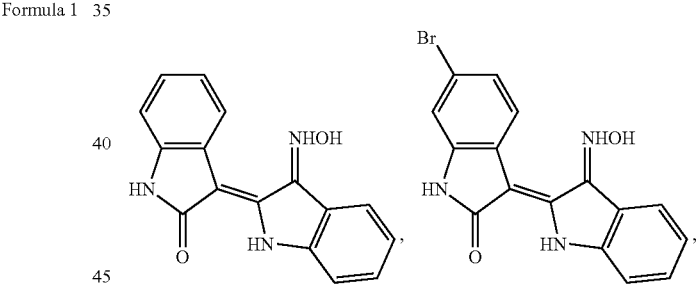

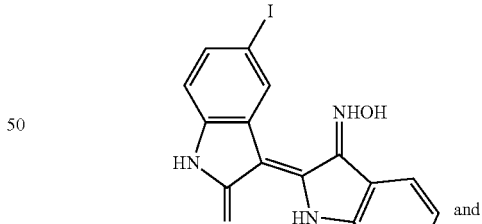

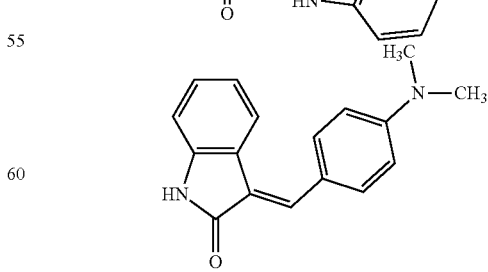

8. The method according to claim 1, wherein the compound of Formula 1 is:

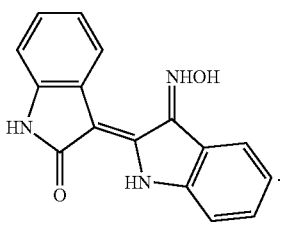

9. The method according to claim 8, wherein the compound of Formula 3 is:

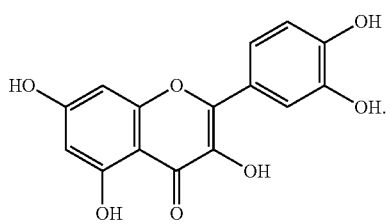 [SMILES: O=c1c(O)c(-c2ccc(O)c(O)c2)oc2cc(O)cc(O)c12]

10. The method according to claim 9, wherein the composition comprises from 0.1 ng/mL to 100 mg/mL of the compound of Formula 3 and from 0.1 ng/mL to 100 mg/mL of the compound of Formula 1.

11. The method according to claim 10, wherein the composition comprises the compound of Formula 3 and the compound of Formula 1 in a molar ratio from 1:1000 to 1000:1.

12. The method according to claim 11, wherein the composition is formulated as an ophthalmic composition.

13. The method according to claim 8, wherein the compound of Formula 3 is:

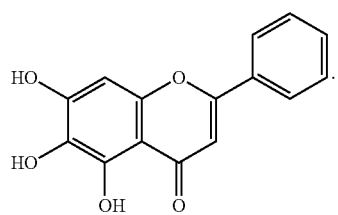 [SMILES: O=c1cc(-c2ccccc2)oc2cc(O)c(O)c(O)c12]

14. The method according to claim 13, wherein the composition comprises from 0.1 ng/mL to 100 mg/mL of the compound of Formula 3 and from 0.1 ng/mL to 100 mg/mL of the compound of Formula 1.

15. The method according to claim 14, wherein the composition comprises the compound of Formula 3 and the compound of Formula 1 in a molar ratio from 1:1000 to 1000:1.

16. The method according to claim 15, wherein the composition is formulated as an ophthalmic composition.

17. The method according to claim 1, wherein the compound of Formula 3 is selected from the group consisting of:

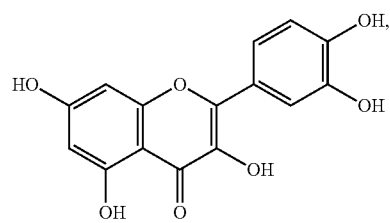

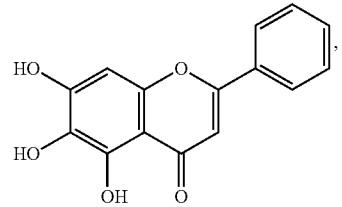 [SMILES: O=c1cc(-c2ccccc2)oc2cc(O)c(O)c(O)c12]

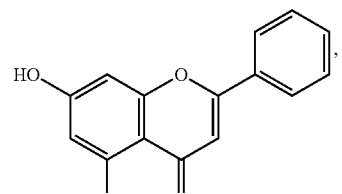

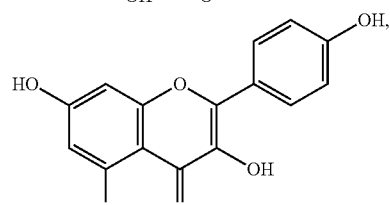

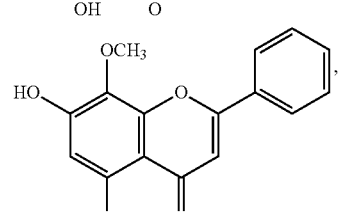

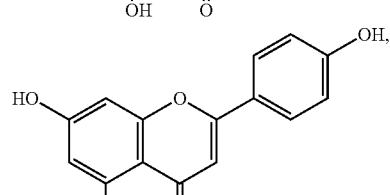

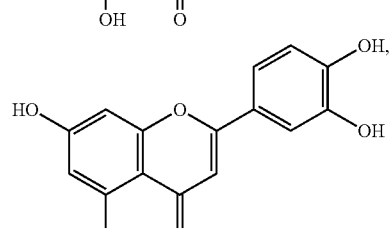

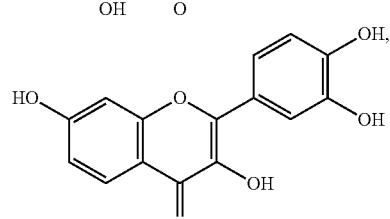

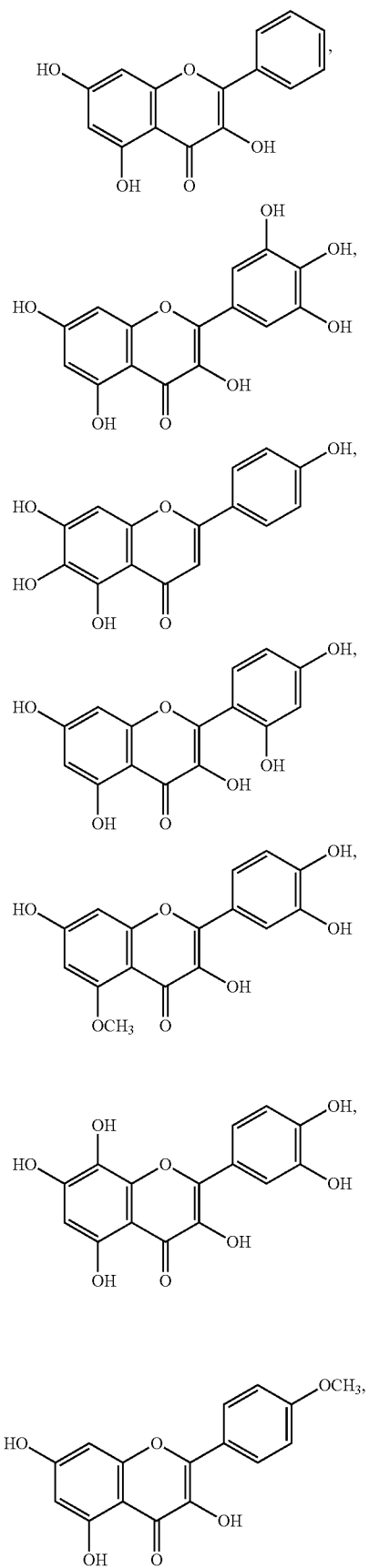
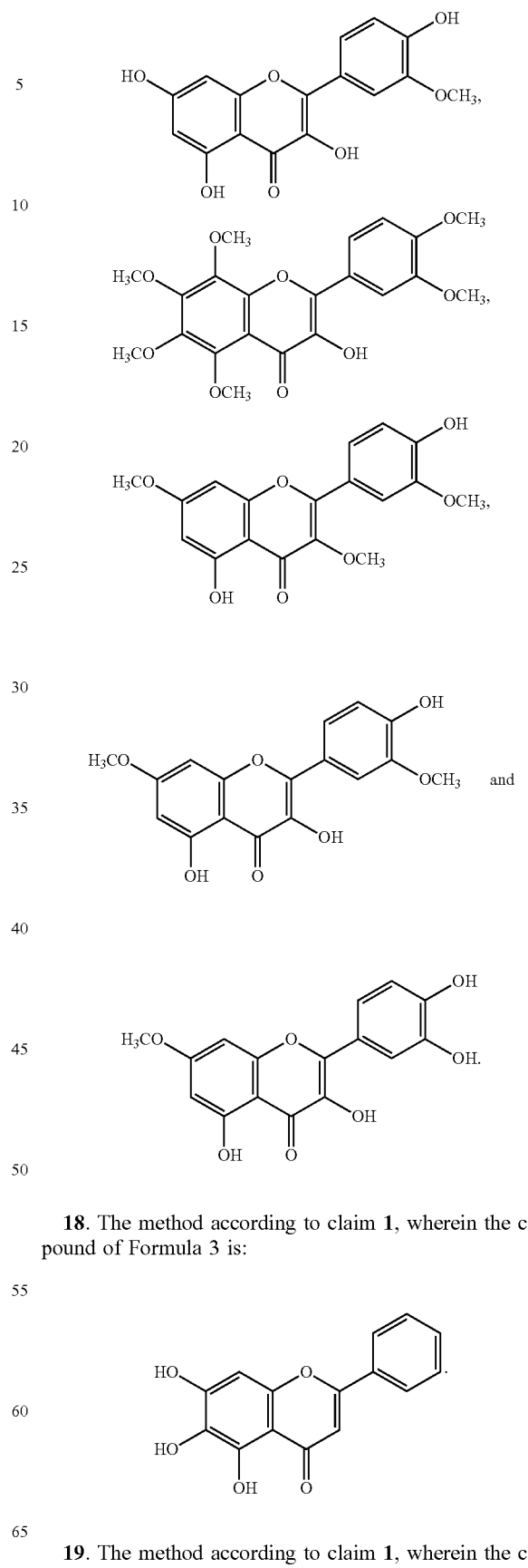
18. The method according to claim 1, wherein the compound of Formula 3 is:
19. The method according to claim 1, wherein the compound of Formula 3 is:

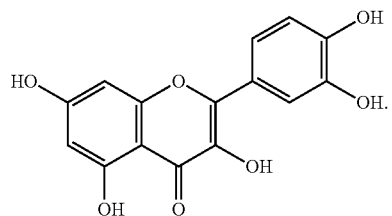 [SMILES: O=c1c(O)c(-c2ccc(O)c(O)c2)oc2cc(O)cc(O)c12]
* * * * *

SEQUENCE LISTING

```
<160> NUMBER OF SEQ ID NOS: 10

<210> SEQ ID NO 1
<211> LENGTH: 22
<212> TYPE: DNA
<213> ORGANISM: Mus musculus

<400> SEQUENCE: 1
tcagcaacaa cataagcgtc at                                              22

<210> SEQ ID NO 2
<211> LENGTH: 24
<212> TYPE: DNA
<213> ORGANISM: Mus musculus

<400> SEQUENCE: 2
gacctcaaac ttggcaatac tcat                                            24

<210> SEQ ID NO 3
<211> LENGTH: 24
<212> TYPE: DNA
<213> ORGANISM: Mus musculus
```

```
<400> SEQUENCE: 3
ggcctccctc tcatcagttc tatg                                          24

<210> SEQ ID NO 4
<211> LENGTH: 18
<212> TYPE: DNA
<213> ORGANISM: Mus musculus

<400> SEQUENCE: 4
gtttgctacg acgtgggc                                                 18

<210> SEQ ID NO 5
<211> LENGTH: 24
<212> TYPE: DNA
<213> ORGANISM: Mus musculus

<400> SEQUENCE: 5
agtcaattcc agaaaccgct atga                                          24

<210> SEQ ID NO 6
<211> LENGTH: 19
<212> TYPE: DNA
<213> ORGANISM: Mus musculus

<400> SEQUENCE: 6
tagggaaggc cgtggttgt                                                19

<210> SEQ ID NO 7
<211> LENGTH: 21
<212> TYPE: DNA
<213> ORGANISM: Mus musculus

<400> SEQUENCE: 7
agtgaaggca gcagcgatca t                                             21

<210> SEQ ID NO 8
<211> LENGTH: 17
<212> TYPE: DNA
<213> ORGANISM: Mus musculus

<400> SEQUENCE: 8
cgccaaggga gttaaag                                                  17

<210> SEQ ID NO 9
<211> LENGTH: 20
<212> TYPE: DNA
<213> ORGANISM: Mus musculus

<400> SEQUENCE: 9
cgagaatggg aagcttgtca                                               20

<210> SEQ ID NO 10
<211> LENGTH: 24
<212> TYPE: DNA
<213> ORGANISM: Mus musculus

<400> SEQUENCE: 10
agacaccagt agactccacg acat                                          24
```